US012023361B2

(12) United States Patent
Tsai et al.

(10) Patent No.: US 12,023,361 B2
(45) Date of Patent: Jul. 2, 2024

(54) METHOD FOR PROMOTING HAIR GROWTH

(71) Applicant: GENMONT BIOTECH INC., Tainan (TW)

(72) Inventors: Wan-hua Tsai, Kaohsiung (TW); Chia-hsuan Chou, Tainan (TW); Tsuei yin Huang, Tainan (TW); Ying-ju Chiang, Tainan (TW); Ching-gong Lin, Kaohsiung (TW)

(73) Assignee: GENMONT BIOTECH INC., Tainan (TW)

( * ) Notice: Subject to any disclaimer, the term of this patent is extended or adjusted under 35 U.S.C. 154(b) by 38 days.

(21) Appl. No.: 17/658,635

(22) Filed: Apr. 8, 2022

(65) Prior Publication Data

US 2023/0190832 A1 Jun. 22, 2023

(30) Foreign Application Priority Data

Nov. 26, 2021 (TW) .................................. 110144288

(51) Int. Cl.
  *A61K 35/747* (2015.01)
  *A61P 17/14* (2006.01)
  *C12N 1/20* (2006.01)
  *C12R 1/225* (2006.01)

(52) U.S. Cl.
  CPC ............ *A61K 35/747* (2013.01); *A61P 17/14* (2018.01); *C12N 1/20* (2013.01); *C12N 1/205* (2021.05); *C12R 2001/225* (2021.05)

(58) Field of Classification Search
  CPC .... A61K 35/747; A61K 35/74; A61K 35/741; A61K 35/742; A61P 17/14; C12N 1/20; C12R 2001/225
  See application file for complete search history.

(56) References Cited

U.S. PATENT DOCUMENTS

| 2011/0014248 A1* | 1/2011 | Castiel | A61P 17/14 424/93.46 |
| 2018/0256651 A1* | 9/2018 | Chen | A61P 37/00 |

FOREIGN PATENT DOCUMENTS

| KR | 20210055901 | * | 5/2021 | ............... C12N 1/20 |
| KR | 1020210055901 A | | 5/2021 | |
| TW | 201832772 A | | 9/2018 | |

OTHER PUBLICATIONS

Almeida et al., An Bras Dermatol., 2013, 88(6 Suppl 1):S29-31 (Year: 2013).*
Bain et al., British Journal of Dermatology, 2020, 182:130-137 (Year: 2020).*
Taiwanese Office Action issued in corresponding Taiwanese Patent Application No. 110144288 dated Oct. 25, 2022, pp. 1-4.

* cited by examiner

*Primary Examiner* — Qing Xu
(74) *Attorney, Agent, or Firm* — PV IP PC; Wei Te Chung; Zhigang Ma

(57) ABSTRACT

A method for promoting hair growth is disclosed. The method comprises a step of administering *Lactobacillus paracasei* GMNL-653 to a subject who needs to increase hair volume at a dose of $1.25 \times 10^8$ to $5 \times 10^8$ cells/ml/day, and the *Lactobacillus paracasei* GMNL-653 was deposited at the China Center for Type Culture Collection located at Wuhan University, Wuhan 430072 P.R. China on Apr. 25, 2016 under an accession number CCTCC NO. M 2016226.

2 Claims, 41 Drawing Sheets

Specification includes a Sequence Listing.

METHOD FOR PROMOTING HAIR GROWTH

CROSS-REFERENCE TO RELATED APPLICATIONS

The present application claims the benefit of Taiwan patent serial number 110144288 filed Nov. 26, 2021, the disclosure of which is incorporated herein by reference.

FIELD OF INVENTION

The present disclosure relates to a strain of *Lactobacillus paracasei* for promoting hair growth, and in particular to a strain of *Lactobacillus paracasei* GMNL-653 for promoting hair growth, hair product having same, and use thereof.

BACKGROUND OF INVENTION

Ultraviolet light, smoking, air pollutants, chemical dyes, microbial changes, etc. may increase peroxides of scalps and hair fibers, generate oxidative stress, accelerate aging of scalps, and cause symptoms such as graying, baldness, and dandruff.

Growth cycles of hair follicles have three phases: anagen phase, catagen phase, and telogen phase. A main reason for excessive hair shedding is that the hair follicles cannot normally enter the anagen (growth) phase after hair shedding. Some effective hair-strengthening substances can stimulate scalp keratinocytes or hair follicle cells to produce some growth factors, such as insulin-like growth factor-1 (IGF-1), insulin-like growth factor-1 receptor (IGF-1R), keratinocyte growth factor (KGF), vascular endothelial growth factor (VEGF), transforming growth factor-β (TGF-β), which have effects of promoting hair growth.

Microbiota balance of scalp hair follicles is important for scalp health. For example, acne vulgaris is caused by increase of *Propionibacterium acnes* (*P. acnes*) RT4/RT5 on patient's scalps, alopecia areata is caused by increase of *P. acnes* and decrease of *Staphylococcus epidermidis* (*S. epidermidis*) on patient's scalps, male-pattern alopecia is caused by increase of *P. acnes* and *Malassezia restricta* (*M. restricta*) on patient's scalps, dandruff is caused by increase of *S. epidermidis* and *Malassezia* on patient's scalps, and folliculitis decalvans is caused by increase of *Staphylococcus aureus* (*S. aureus*) and *P. acnes* on patient's scalps. In addition, studies on the microbiome of a human scalp with dandruff show that *M. restricta* is adverse yeast, and *Malassezia globosa* (*M. globosa*) is beneficial yeast, which belong to the same genus, i.e., *Malassezia*. However, general anti-dandruff shampoos, such as containing zinc pyrithione (ZP), may inhibit growth of all *Malassezia* bacteria, resulting in imbalance of scalp microbiota after long-term use, which has little benefit in control of dandruff. *Malassezia furfur* (*M. furfur*) is a known adverse bacteria existing on scalps, and a biofilm thereof is an important pathogenic factor. Specifically, *M. furfur* is protected from bacteriostatic agents by formation of the biofilm which is an important defense mechanism for pathogens. Thus, it is important to prevent skin pathogens from forming biofilms which are causes of the disease.

As mentioned above, conventional hair products still need to be improved in terms of promoting scalp health, including effects of promoting hair growth.

SUMMARY OF INVENTION

Technical Problems

A main purpose of the present disclosure is to provide a strain of *Lactobacillus paracasei* that promotes hair growth, so as to achieve the effects of promoting hair growth.

Technical Solutions

In order to achieve the foregoing purpose of the present disclosure, the present disclosure provides a method for promoting hair growth, comprising a step of administering a strain of *Lactobacillus paracasei* GMNL-653 to a subject who needs to increase hair volume at a dose of $1.25 \times 10^8$ to $5 \times 10^8$ cells/ml/day, and the *Lactobacillus paracasei* GMNL-653 was deposited at the China Center for Type Culture Collection located at Wuhan University, Wuhan 430072 P.R. China on Apr. 25, 2016 under an accession number CCTCC NO. M 2016226 under the Budapest Treaty.

According to an embodiment of the present disclosure, an effective dose of the strain of *Lactobacillus paracasei* GMNL-653 ranges from $1.25 \times 10^8$ to $5 \times 10^8$ cells/ml.

According to an embodiment of the present disclosure, the strain of *Lactobacillus paracasei* GMNL-653 is a dead bacteria strain.

In order to achieve the foregoing purpose of the present disclosure, the present disclosure further provides a hair product for promoting hair growth, comprising: the strain of *Lactobacillus paracasei* for promoting hair growth as mentioned above; and a surfactant.

According to an embodiment of the present disclosure, an effective dose of the hair product ranges from $1.25 \times 10^8$ to $5 \times 10^8$ cells/ml.

According to an embodiment of the present disclosure, the strain of *Lactobacillus paracasei* GMNL-653 is a dead bacteria strain.

In order to achieve the foregoing purpose of the present disclosure, the present disclosure further provides a use of the strain of *Lactobacillus paracasei* for promoting hair growth as claimed in claim 1 in preparing a hair product for promoting hair growth.

According to an embodiment of the present disclosure, the strain of *Lactobacillus paracasei* GMNL-653 in the hair product is administrated to a subject who needs to increase hair volume at a dose of $1.25 \times 10^8$ to $5 \times 10^8$ cells/ml/day.

According to an embodiment of the present disclosure, a number of days of administration ranges from 1 to 3 months.

Beneficial Effects:

The strain of *Lactobacillus paracasei* for promoting hair growth of the present disclosure can resist scalp aging and promote human skin fibroblasts and keratinocytes to produce hair growth factors, such as IGF-1, VEGF, KGF, and can also regulate scalp follicle microflora, such as increasing beneficial bacteria on scalps (e.g., *Malassezia globosa* (*M. globosa*)), inhibiting adverse bacteria on scalps (e.g., *Propionibacterium acnes* (*P. acnes*) and *Malassezia restricta* (*M. restricta*)), thereby promoting hair regeneration, strengthening hair roots, controlling oiliness and dandruff, and maintaining healthy scalp environments.

DESCRIPTION OF DRAWINGS

In order to more clearly illustrate the above contents of the present disclosure, the following is a detailed description of the preferred embodiments with reference to the accompanying drawings:

FIG. 1A and FIG. 1B show effects of GMNL-653 against senescence of skin cells caused by hydrogen peroxide, wherein FIG. 1A shows ratios of aging cells in each group; and FIG. 1B shows a comparison of anti-aging capacities of different *Lactobacillus paracasei* strains.

FIG. 2A is a scanning electron microscope image of pathogenic bacteria coaggregated by GMNL-653; FIG. 2B shows an evaluation of an ability of GMNL-653 against *Staphylococcus aureus* (*S. aureus*) adhering to cells by using a cell-based platform; FIG. 2C shows effects of treatments of lipoteichoic acid (LTA) isolated from GMNL-653 on formation of biofilms by *Malassezia furur* (*M. furur*); FIG. 2D shows effects of treatments of LTA isolated from GMNL-653 on formation of biofilms by *S. aureus*, in which data are statistically analyzed by t-test, and a symbol "*" indicates a statistical difference compared with a control group ($P<0.05$).

FIG. 3A shows the level of IGF-1R; FIG. 3B shows the level of VEGF; FIG. 3C shows the level of IGF-1; and FIG. 3D shows the level of KGF, in which data are statistically analyzed by t-test; and a symbol "*" indicates a statistical difference compared with the control group ($P<0.05$).

FIG. 4A shows the level of IGF-1R; FIG. 4B shows the level of VEGF; and FIG. 4C shows the level of IGF-1, in which data are statistically analyzed by t-test; and a symbol "*" indicates a statistical difference compared with the control group ($P<0.05$).

FIG. 5A and FIG. 5B show analysis scalp areas and items of the human clinical trial using a control group shampoo and an experimental group shampoo (containing the strain of *Lactobacillus paracasei* promoting hair growth of the present disclosure), respectively, wherein FIG. 5A shows the detection points on the scalp in front, middle, and back areas (left), a device for detecting scalp oil counts (middle), and a device for detecting hair volume (right); FIG. 5B shows use of whole head dandruff tape (top left) and microbiota sampling (top right) for analysis, in which a subject's scalp was pasted with a tape for collecting dandruff, the dandruff area (bottom) is quantified by Image J drawing software, and scalp microbiota is detected by Q-PCR.

FIG. 6A to FIG. 6C show effects of the experimental group shampoo on scalp oil counts of the subjects, wherein FIG. 6A shows oil counts of all of the subjects (N=20); FIG. 6B shows oil counts of the subjects with oily scalp (N=7); and FIG. 6C shows oil counts of the subjects with non-oily scalp (N=13), in which a calculation method is to sum up the scalp oil counts of the top (middle), back, and front of the head; data are statistically analyzed by paired sample t-test; a symbol "*" indicates a statistical difference compared with start time (0 months (M)) ($P<0.05$); and a symbol "#" indicates a statistical difference compared with the use of the control group shampoo for 1 month ($P<0.05$).

FIG. 7A to FIG. 7C show effects of the experimental group shampoo on the subjects' dandruff, wherein FIG. 7A shows the quantitative data of the dandruff tapes of all of the subjects (N=18); FIG. 7B shows the quantitative data of the dandruff tapes of those with more dandruff (N=8); FIG. 7C shows the quantitative data of the dandruff tapes of those with less dandruff (N=10); in which the data are statistically analyzed by paired sample t-test, a symbol "*" indicates that there is a statistical difference compared with start time (0M) ($P<0.05$), and a symbol "#" indicates that there is a statistical difference compared with the use of the control group shampoo for 1 month ($P<0.05$).

FIG. 8A to FIG. 8C show effects of the experimental group shampoo on the subjects' hair volume, wherein FIG. 8A shows changes in the hair volume of all subjects (N=19); FIG. 8B shows changes in the hair volume of those with less hair volume (N=10); FIG. 8C shows changes in the hair volume of those with more hair volume (N=9), and the calculation method is to calculate the average hair volume on the top (middle), back, and front of the head, in which the data are statistically analyzed by paired sample t-test, a symbol "*" indicates that there is a statistical difference compared with start time (0M) ($P<0.05$), and a symbol "#" indicates that there is a statistical difference compared with the use of the control group shampoo for 1 month ($P<0.05$).

FIG. 9A to FIG. 9E show effects of the experimental group shampoo on the subjects' scalp microbiota, wherein FIG. 9A to FIG. 9E show the relative content is expressed as $2^{-\Delta CT}$ after calculation of different strains and total strains, in which the data are statistically analyzed by paired sample t-test, a symbol "*" indicates that there is a statistical difference compared with start time (0M) ($P<0.05$), and a symbol "#" indicates that there is a statistical difference compared with the use of the control group shampoo for 1 month ($P<0.05$).

FIG. 10A to FIG. 10F show effects of GMNL-653 shampoo on the change in the microbiota of those with more dandruff and those with less dandruff, wherein FIG. 10A, FIG. 10C, and FIG. 10E show different changes in the microbiota of those with more dandruff; FIG. 10B, FIG. 10D, and FIG. 10F show different changes in the microbiota of those with less dandruff; and the relative content is expressed as $2^{-\Delta CT}$ after calculation of different strains and total strains, in which the data are statistically analyzed by paired sample t-test, a symbol "*" indicates that there is a statistical difference compared with start time (0M) ($P<0.05$), and a symbol "#" indicates that there is a statistical difference compared with the use of the control group shampoo for 1 month ($P<0.05$).

DETAILED DESCRIPTION OF PREFERRED EMBODIMENTS

Figure 1A:
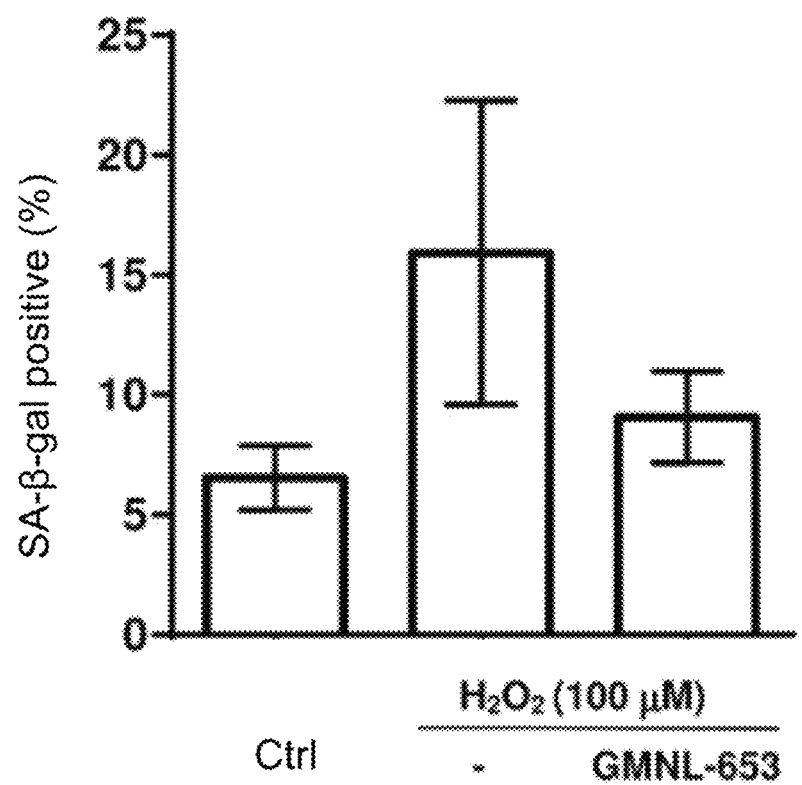

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As used herein, the singular form "a", "an" and "the" include plural references unless the context clearly dictates otherwise. The numerical range (such as 10% to 11% of A) includes the upper and lower limits (i.e., 10%≤A≤11%) unless otherwise specified. If the numerical range does not define the lower limit (such as less than 0.2% of B, or below 0.2% of B), it means that the lower limit may be 0 (i.e., 0%≤B≤0.2%). The above terms are made for the purposes of describing and illustrating the present disclosure and should not be taken in a limiting sense.

In an embodiment of the present disclosure, there is provided a method for promoting hair growth, comprising a step of administering a strain of Lactobacillus paracasei GMNL-653 to a subject who needs to increase hair volume at a dose of $1.25 \times 10^8$ to $5 \times 10^8$ cells/ml/day, and the Lactobacillus paracasei GMNL-653 was deposited at the China Center for Type Culture Collection located at Wuhan University, Wuhan 430072 P.R. China on Apr. 25, 2016 under an accession number CCTCC NO. M 2016226 under the Budapest Treaty.

The strain of Lactobacillus paracasei GMNL-653 in the above embodiment is one of multiple isolates obtained through screening from a human intestinal tract. PCR was performed to replicate the 16S rDNA fragments of multiple isolates by using the primers in Table 1 (SEQ ID NO: 1 and SEQ ID NO: 2), and then sequencing was performed. After the sequencing was completed, a gene sequence of the 16S rDNA of one of the isolates was obtained (SEQ ID NO: 3). Subsequently, a comparison result from the NCBI website shows that the 16S rDNA sequence of the isolate (SEQ ID NO: 3) and the 16S rDNA sequence of Lactobacillus paracasei is similar, with over 99% of the similarity, Thus, the strain GMNL-653 is determined to be Lactobacillus paracasei.

TABLE 1

| primer | sequence ID number | sequence |
| --- | --- | --- |
| PAF | SEQ ID NO: 1 | AGA GTT TGA TCC TGG CTC AG |
| 536R | SEQ ID NO: 2 | GTA TTA CCG CGG CTG CTG |

Preferably, in the embodiment, the strain of Lactobacillus paracasei GMNL-653 is dead bacterial strain, and an effective dose of the strain of Lactobacillus paracasei GMNL-653 ranges from $1.25 \times 10^8$ to $5 \times 10^8$ cells/ml, such as $1.25 \times 10^8$, $1.5 \times 10^8$, $2 \times 10^8$, $2.5 \times 10^8$, $3 \times 10^8$, $3.5 \times 10^8$, $4 \times 10^8$, $4.5 \times 10^8$, and $5 \times 10^8$ cells/ml.

In an embodiment of the present disclosure, there is further provided a hair product promoting hair growth, including the aforementioned strain of Lactobacillus paracasei promoting hair growth; and a surfactant, such as sodium laureth sulfate or cocoamidopropyl betaine. In the embodiment, the hair product is shampoo. Certainly, the present disclosure is not limited to this. In other embodiments, the hair product may be a hair conditioner or a hair treatment. In addition, other products used for scalp care and repair, such as scalp care lotion, may include the aforementioned strain of Lactobacillus paracasei promoting hair growth.

Preferably, in the embodiment of the aforementioned hair product, the strain of Lactobacillus paracasei GMNL-653 is dead bacterial strain, and an effective dose of the strain of Lactobacillus paracasei GMNL-653 ranges from $1.25 \times 10^8$ to $5 \times 10^8$ cells/ml, such as $1.25 \times 10^8$, $1.5 \times 10^8$, $2 \times 10^8$, $2.5 \times 10^8$, $3 \times 10^8$, $3.5 \times 10^8$, $4 \times 10^8$, $4.5 \times 10^8$, and $5 \times 10^8$ cells/ml.

In an embodiment of the present disclosure, there is further provided a use of the aforementioned strain of Lactobacillus paracasei promoting hair growth in a preparation of a hair product promoting hair growth.

Specifically, in the embodiment, the strain of Lactobacillus paracasei GMNL-653 in the composition of the hair product is administrated to a subject in needs of increasing the hair volume at a dose of $1.25 \times 10^8$ to $5 \times 10^8$ cells/ml/day for 1 to 3 months.

The term "subject" herein refers to a mammal in needs of promoting an effect of hair growth. Generally, the "subject" refers to a human being. However, in other embodiments, the term "subject" may be a non-human mammal, such as a non-human primate, dog, cat, cow, horse, rabbit, pig, and so on.

In order to verify that the probiotic composition of the present disclosure possesses the effect of promoting hair growth, the following experiments were conducted.

In the following experiments, the experimental methods without specific conditions are selected according to conventional methods and conditions, or according to the instructions of kits.

Estimation of an Ability of the GMNL-653 Lysate for Anti-Aging:

The Hs68 cells were cultured in a 12-well cell culture plate, 100 μM hydrogen peroxide ($H_2O_2$) was given to stimulate cells for 1 hour, and then the cells were transferred to serum-containing cell culture medium for continuous culture for 4 days. The lysate groups of different lactic acid strains: the Hs68 cells were treated with the serum-free cell culture medium containing 100 μM $H_2O_2$ and the lysates of different tested lactic acid strains for 1 hour, and then the cells were transferred to 10% serum-supplemented cell culture medium containing the lysates of tested lactic acid strains for continuous culture for 4 days.

After the experiment, fixation and senescence-associated β-galactosidase (SA-β-gal) staining were performed, and the percentage of cells stained blue was counted. The higher the percentage of SA-β-gal-positive cells is, the greater the degree of cell aging is. A formula for calculating the anti-aging ratio is as follows. The ability of inhibiting hydrogen peroxide-caused cell aging was calculated by the ratio of the difference of cell aging percentage between hydrogen peroxide group (Sham) and lactic acid bacteria group (Test) divided by the difference of cell aging percentage between hydrogen group (Sham) and control group (Control). The higher the ratio is, the better the ability to slow down cell aging is.

$$\text{the ability of inhibiting hydrogen peroxide-caused cell aging}(\%) = \frac{\text{difference of cell aging percentage (Sham} - \text{Test)}}{\text{difference of cell aging percentage (Sham} - \text{Control)}} \times 100\%$$

Interaction Between GMNL-653 and Skin Pathogenic Bacteria:

Preparation of Probiotics and Pathogenic Bacteria:

Probiotic dead bacteria preparation steps: *Lactobacillus paracasei* GMNL-653, BCRC 910953 or BCRC 910626 were inoculated from frozen glycerol bacterial stocks into 1 ml of MRS broth, and were cultured at 37° C. under aerobic conditions for 20 hours. On the next day, 15 ul of overnight culture broth was taken to 1.5 ml of MRS broth at the 1:100 inoculation ratio, incubated for 20 hours under aerobic conditions at 37° C., and washed once with PBS. A number of bacteria was estimated with OD 600 nm, and the number of bacteria was adjusted to $2\times10^9$ to $1\times10^{10}$ cells/ml. Then, bacteria was heated and sterilized by autoclave (121° C. for 15 minutes), followed by cooling down to room temperature. GMNL-653 lysate and lipoteichoic acid were prepared by using a bacteriolytic device to break the bacteria. After centrifugation, serial extraction procedures were conducted. A concentration of the GMNL-653 lysate was determined by protein quantification assay. Quantitation of lipoteichoic acid was mainly based on the dry weight after purification. About 18.73 mg of lipoteichoic acid can be purified from $1.6\times10^{13}$ cells/g of GMNL-653.

The pathogenic bacteria *Staphylococcus aureus* (*S. aureus*) (BCRC 11863) were cultured with TSB medium in a general incubator at 37° C., and the probiotics and pathogenic bacteria were reinoculated the next day. A number of the bacteria was adjusted to $2\times10^9$ cfu/ml. The pathogenic bacteria *Malassezia furfur* (*M. furfur*) (BCRC 22243) were streaked onto modified Leeming & Notman agar (MLNA) plates, incubated at 30° C., and then reinoculated every 2 days. Bacteria was scraped from agar plate and resuspended in PBS, and the number of bacteria was adjusted to $2\times10^9$ cell/ml for later use.

Experimental Methods to Observe the Co-Aggregation of Probiotics and Pathogenic Bacteria:

Heat-killed lactic acid bacteria ($2\times10^9$ cells/ml) and pathogenic bacteria ($2\times10^9$ cfu/ml) were mixed at a ratio of 1:1 for 30 minutes. Then, the visible coagglutinated samples were taken out, spread onto the coverslip using cytospin technique (low-speed centrifugation), washed, and then fixed with 2.5% glutaradehyde at room temperature for 1 hour. After rinsing with PBS 3 times, dehydrating was performed, treatments of 40%, 75% and 95% ethanol in increasing concentration for 10 minutes respectively were conducted, and followed by a treatment of 100% ethanol for 20 minutes 3 times. Finally, the coagglutination situation was observed by using a scanning electron microscope (SEM).

Observation of *S. aureus* Attached to Skin Cells Under Optical Microscopes:

Hs68 cells ($1\times10^5$ cells per well) were added into a 24-well cell culture plate containing round glass coverslips (10-mm diameter), and incubated overnight. The lactic acid bacteria and pathogenic bacteria were resuspended in PBS. The number of the lactic acid bacteria was adjusted to $1\times10^{10}$ cfu/ml and heat killing was performed. The number of the pathogenic bacteria was adjusted to $1\times10^{10}$ cfu/ml. The numbers of the lactic acid bacteria and pathogenic bacteria were diluted to $5.6\times10^8$ cfu/ml with serum-free and antibiotic-free DMEM respectively, mixed at a ratio of 1:1, and placed at 37° C. for 0.5 hours. The cells cultured on the glass coverslips overnight were washed twice with PBS, 0.5 ml of GMNL-653 and *S. aureus* premix was added to the wells, and incubated in $CO_2$ incubator for 1 hour. Then, the cells were washed with PBS 3 times and fixed with 1 ml of methanol. The glass coverslips were stained with Giemsa solution for 15 minutes, and washed with deionized water 3 times. Finally, the glass coverslips were mounted on glass microscope slides, and the attachments of pathogenic bacteria on the cells were observed with optical microscopes.

Biofilm Formation and Staining Method:

The numbers of the two pathogenic bacteria were adjusted to $2\times10^8$ cfu/ml, and 0.1 ml of the adjusted pathogenic bacterial solution was transferred to a 96-well cell culture plate. 0.1 ml of different concentrations of LTA extracted from GMNL-653 was added into a 96-well cell culture plate, and co-incubated with pathogenic bacteria at 37° C. for 24-48 hours. The bacteria on plates were carefully rinsed with PBS twice to remove suspended or weakly adsorbed bacteria. The biofilms were fixed with 95% ethanol for 1 minute, stained with 0.1% crystal violet for 15 minutes, and carefully rinsed with PBS at least 3 times. Then, the 96-well cell culture plate was dried in a laminar flow hood. 10% of glacial acetic acid (180 ul/well) was added to wells to dissolve the crystal violet. A measurement of absorbance at OD 595 nm was performed. The higher the absorbance is, the more the biofilms form.

Analysis of Heat-Killed GMNL-653 Dead Bacteria to Promote Skin Cells to Produce Hair Growth-Related Factors:

Human skin fibroblasts (Hs68) (concentration: $1.5\times10^5$ cells/well) or human skin keratinocytes (HaCaT) (concentration: $3\times10^5$ cells/well) were inoculated into 6-well plates, respectively. After overnight incubation, cells were washed twice with PBS, and treated with serum-free medium for 24 hours. Then, different doses of dead bacteria suspensions (0.3125 to $5\times10^8$ cells/ml) were added to cells for 24 hours, and afterwards cell were collected. RNA was extracted from the cell and converted into cDNA. The cDNA was used as a template for the Q-PCR reaction. Each reaction reagent contains 5 microliters of 2× Rotor-Gene SYBR Green PCR Master Mix (QIAGEN), 2 microliters of cDNA, and 3 microliters of 0.66 UM forward (F) and reverse (R) primers. Real-time PCR was performed in the Q-PCR machine. The relative gene expression of targets ($2^{-\Delta\Delta Ct}$) was obtained by the CT value obtained by Q-PCR after subtracting from its own housekeeping gene (β-actin, ACTB), and then subtracting from the target gene expression obtained by the control group.

Scalp Clinical Trial Process:

This clinical trial was registered on the ClinicalTrial.gov website with the accession number NCT04566549. A total of 22 healthy adults (age: 37 ±6.2 years old; gender: 8 males, 14 females) were enrolled. The subjects started using the control group shampoo (without the strain of *Lactobacillus paracasei* promoting hair growth of the present disclosure) for 1 month, and then continued to use the shampoo (experimental group) (containing $5\times10^8$ cells/ml GMNL-653) containing the strain of *Lactobacillus paracasei* promoting hair growth of the present disclosure for 4 months. A frequency of shampoo used by the subjects was 1 time/day or 1 time/2 days, according to personal habits. Analysis of scalp oiliness, hair volume, dandruff content and scalp microbiota was conducted at each time point. Scalp oil content, in the front, middle, and back areas of the head, was conducted by using the Sebumeter® SM 815 (Courage+Khazaka electronic GmbH, Germany). The oil content of the scalp was calculated by summing up values of the front, middle and back regions. The hair number of hair follicle was examined by using a multifunctional skin and hair analyser (Aram TSII, Aramhuvis Co., Ltd., Korea) with a 60× lens. The hair number per unit area in the front, middle, and back regions of the head was further quantified by the software to evaluate changes of hair volume before and after using the test product. The change of hair volume is an average value of the front, middle and back areas. The dandruff content analysis was based on a use of dandruff tapes. A special adhesive tape (D-Squame®, CuDerm, Dallas, TX, USA) was used to collect entire dandruff by an assigned and experienced operator, and Image J was used to calculate a percentage (%) of dandruff area on whole surface of the tape to evaluate the dandruff status.

Microbiome analysis of the whole scalp was conducted by using a sterile cotton swab dipped in 1 ml of modified PBS buffer (PBS with 0.1% Triton X; sterilized at 121° C. for 15 minutes for use), and then sampling the whole scalp. After sampling, the swab head was cut off and put into a 1.5 ml microcentrifuge eppendorf containing 1 ml of sterile water, vortexed for at least 30 seconds, and left at room temperature for 15 minutes. The swab head was taken out after centrifugation at 13000 rpm for 10 minutes and transferred to a new 1.5 ml microcentrifuge eppendorf containing 1 ml of sterile water. The swab head was rotated, wrung out and discarded, and all the specimens on the cotton swab were dissolved in sterile water. Then, the samples in above-mentioned 2 microcentrifuge eppendorfs were pooled and centrifuged at 13000 rpm for 5 minutes. The supernatant was removed, and the pellet was left for bacterial DNA extraction (Quick-DNA Fungal/Bacterial Kit). The DNA extracted above was used as a template for Q-PCR amplification. Each reaction reagent contains 5 microliters of 2× Rotor-Gene SYBR Green PCR Master Mix, 2 microliters of DNA extracted from scalp, and 3 microliters of 0.66 μM forward (F) and reverse (R) primer. Real-time PCR was performed in the Q-PCR machine. The relative expression amount (2−ΔCt) of following relevant microbiota was calculated by subtracting the CT value of target bacteria from that of total bacteria.

Figure 1B:
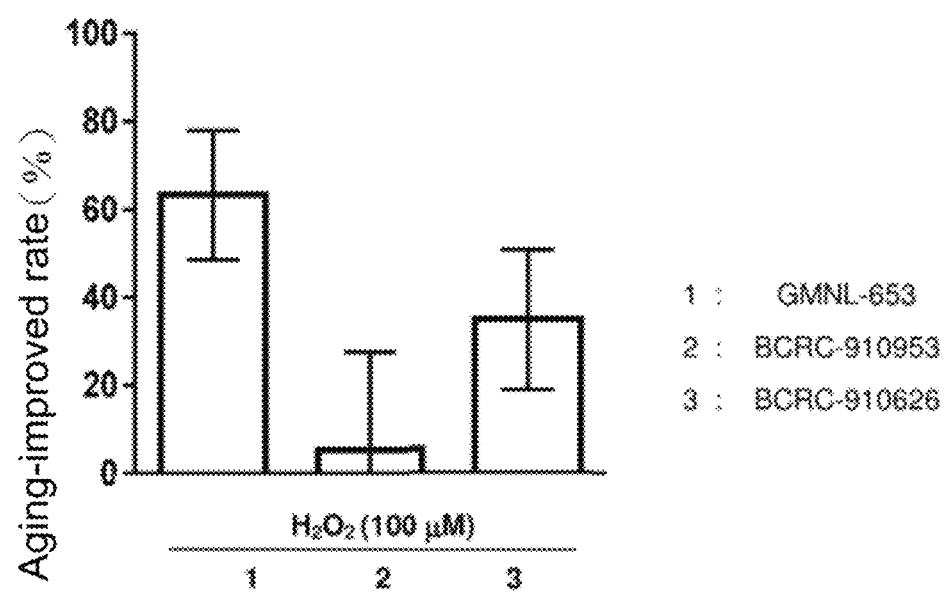

Experimental Results:

UV light or air pollution can generate oxidative stress on the skin and accelerate aging of scalps. Therefore, the ability of lysate of the strain of *Lactobacillus paracasei* promoting hair growth in protecting the scalps from aging caused by oxidative stress was evaluated herein. The content of β-galactosidase in skin cells represents the senescence of the skin cells. After staining, the percentage of cells stained blue was counted. The larger the percentage of SA-β-gal-positive cells is, the higher the degree of aging is. In this experiment, 100 μM hydrogen peroxide was used to induce aging of Hs68 cells. The aging of the skin cells caused by oxidative stress can be effectively reduced by the treatment with GMNL-653 lysate (50 μg/ml) (FIG. 1A). In addition, comparing the effects of different *Lactobacillus paracasei*, GMNL-653 was the best (FIG. 1B).

Figure 2A:
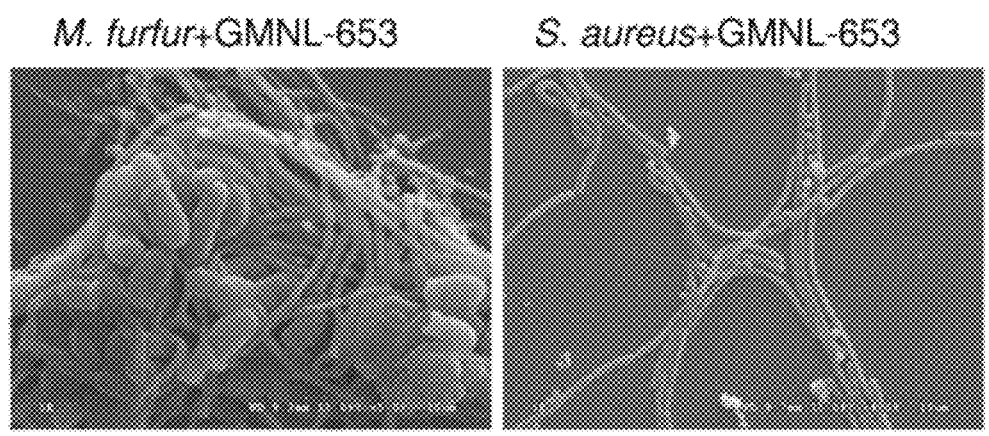
FIG. 2A to FIG. 2D show an interaction between GMNL-653 and dermatopathogens.
Figure 2B:
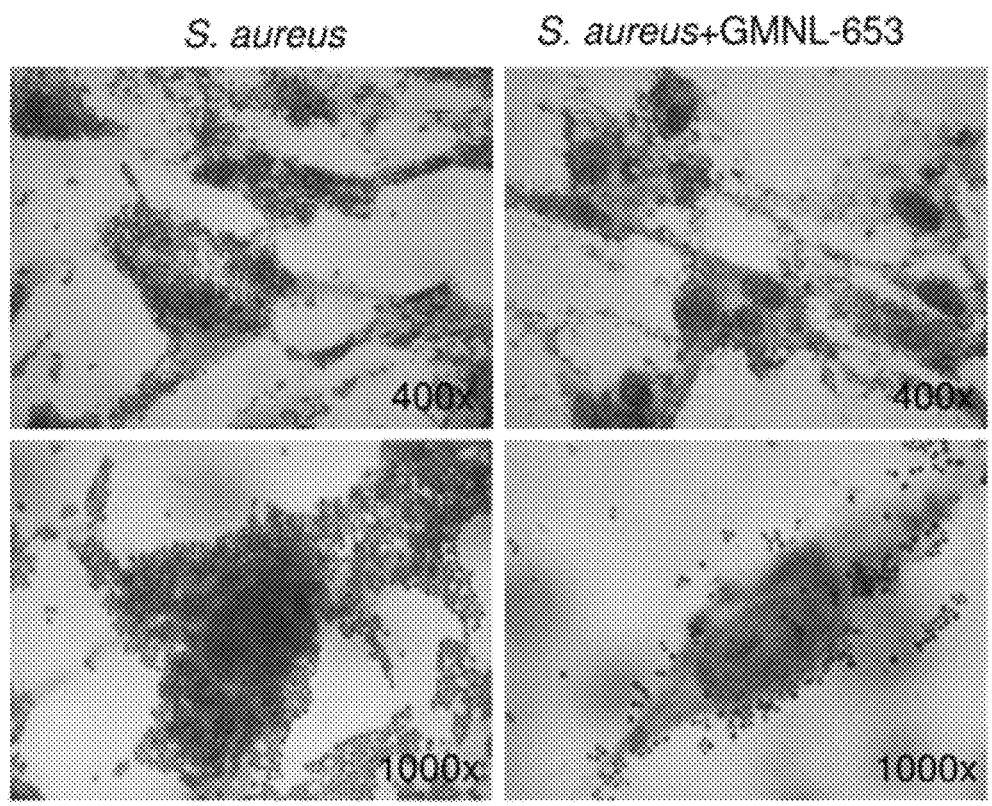
Figure 2C:
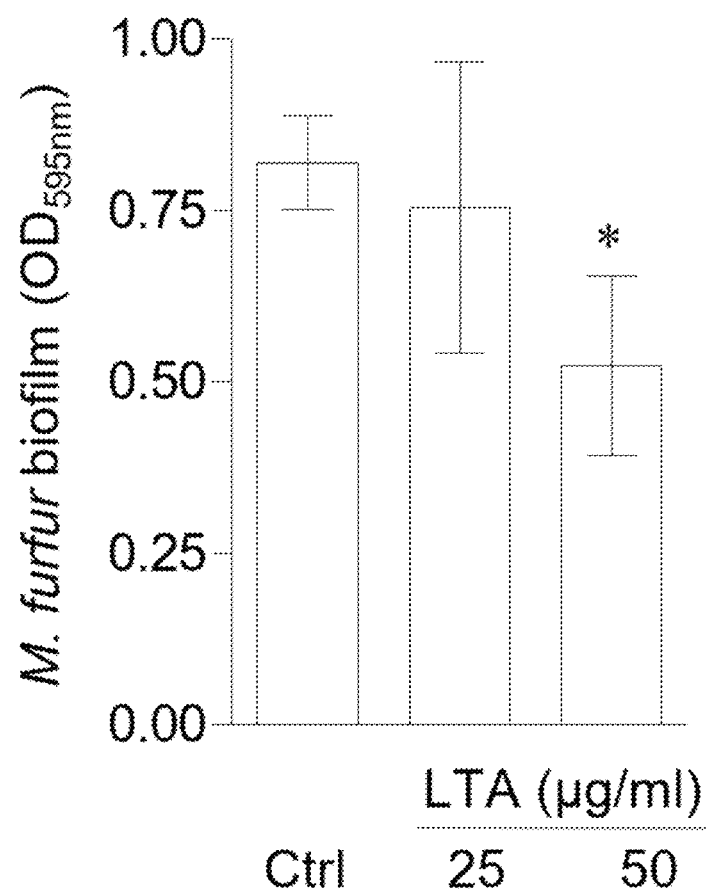
Figure 2D:
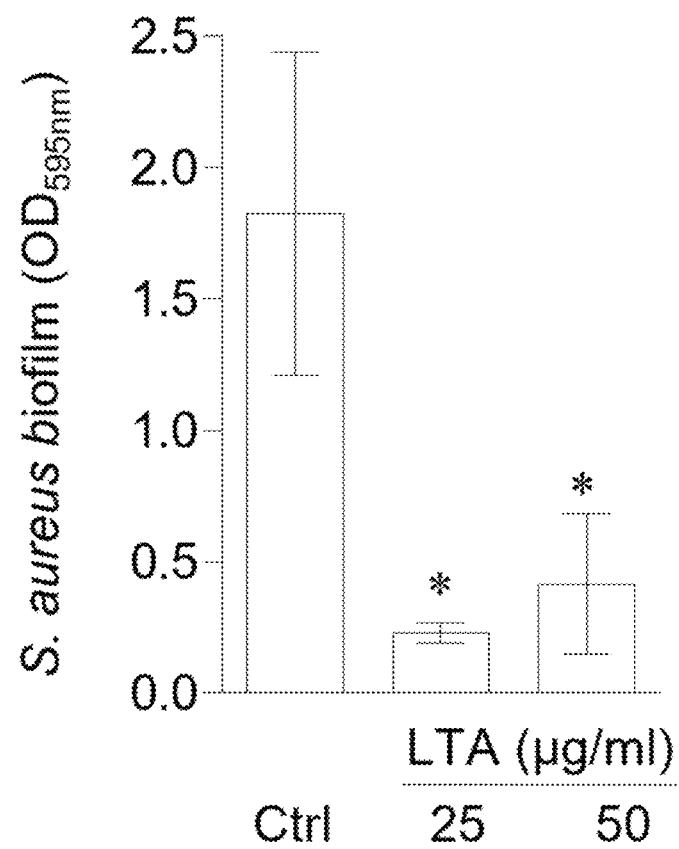

By SEM observation, it was found that scalp pathogenic bacteria *M. furfur* and *S. aureus* can be coaggregated by *Lactobacillus paracasei* GMNL-653 (FIG. 2A), therefore changing skin microbiota could be achieved through coaggregation with pathogens. Further, by the *S. aureus* attachment experiment, it was found that GMNL-653 can obviously inhibit the attachment of *S. aureus* to human skin cells (FIG. 2B), indicating that GMNL-653 can prevent pathogen from attaching to cells after pathogenic bacteria were coaggregated by GMNL-653. In addition, lipoteichoic acid (LTA), a surface substance isolated from GMNL-653, can inhibit the formation of the biofilms of *M. furfur* and *S. aureus* (FIG. 2C, FIG. 2D), so that the purpose of inhibiting the colonization of pathogenic bacteria and skin deterioration can be achieved.

Figure 3A:
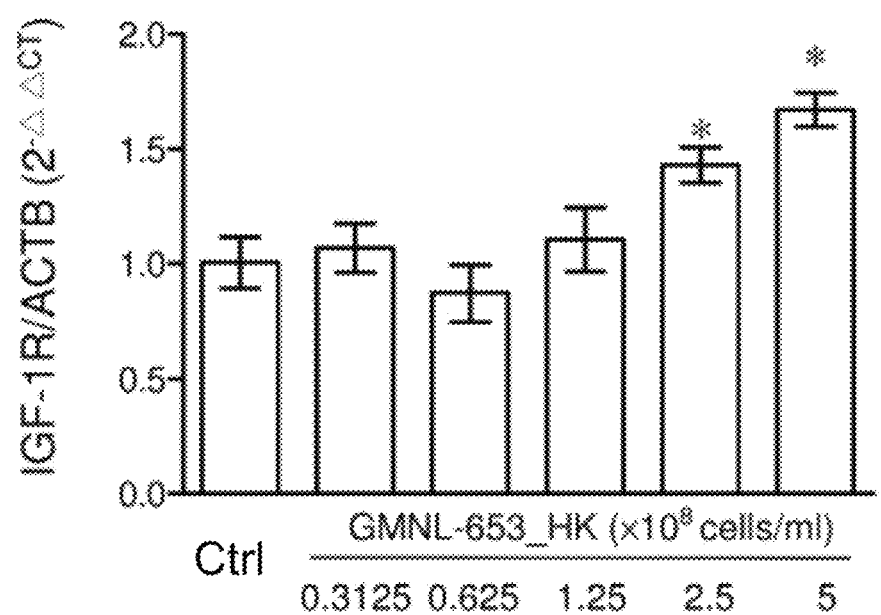
FIG. 3A to FIG. 3D show effects of GMNL-653 on stimulating Hs68 cells to produce hair growth factor, wherein real-time quantitative polymerase chain reaction (Q-PCR) is used to detect content of hair growth factors produced by cells stimulated by GMNL-653, $2^{-\Delta\Delta CT}$ represents a relative expression amount of the target gene when compared with the control group, and ACTB is the internal control gene of each group.
Figure 3B:
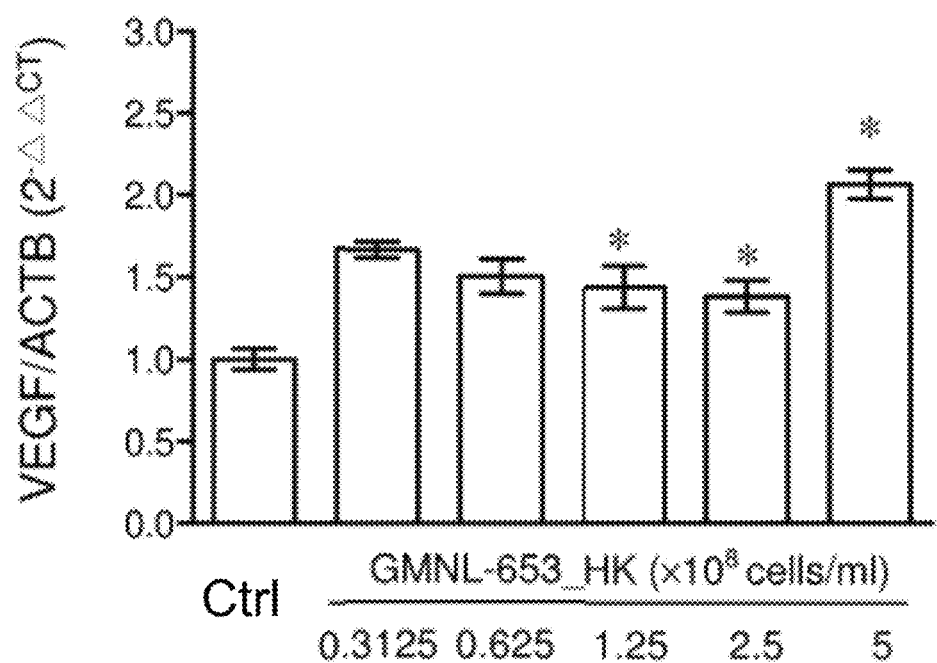
Figure 3C:
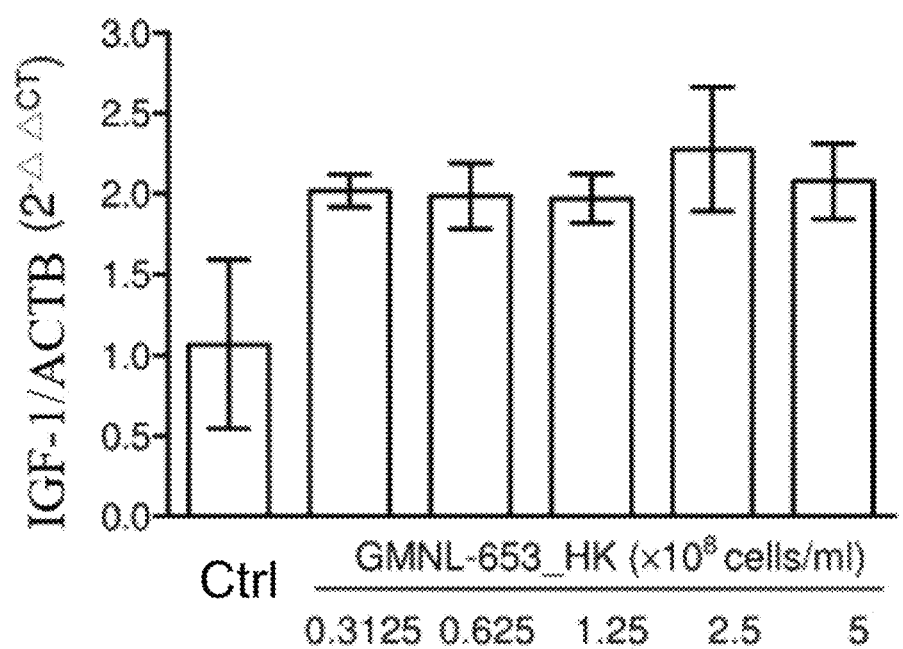
Figure 3D:
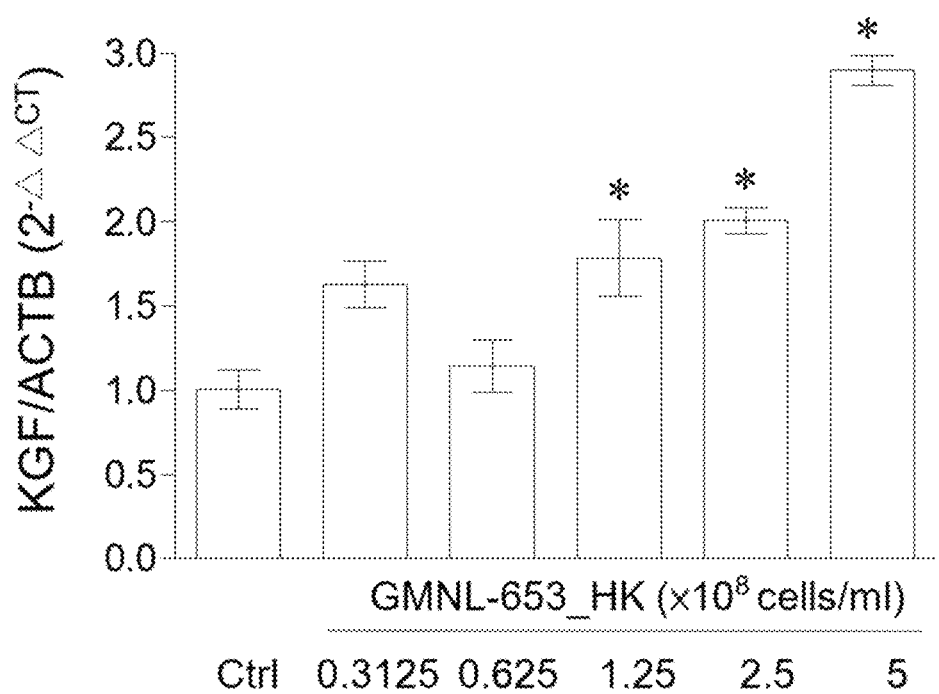
Figure 4A:
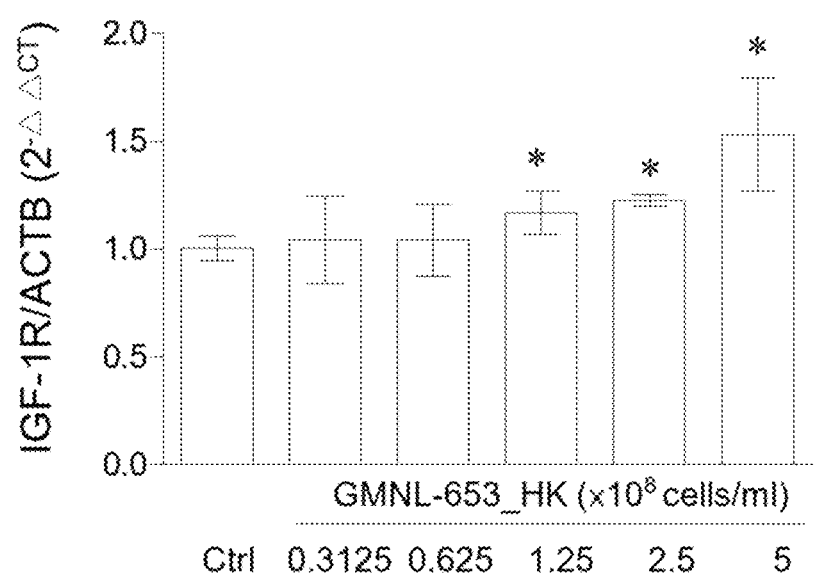
FIG. 4A to FIG. 4C show effects of GMNL-653 on stimulating HaCaT cells to produce hair growth factor, wherein Q-PCR is used to detect content of hair growth factors produced by cells stimulated by GMNL-653, $2^{-\Delta\Delta CT}$ represents a relative expression amount of the target gene when compared with the control group, and ACTB is the internal control gene of each group.
Figure 4B:
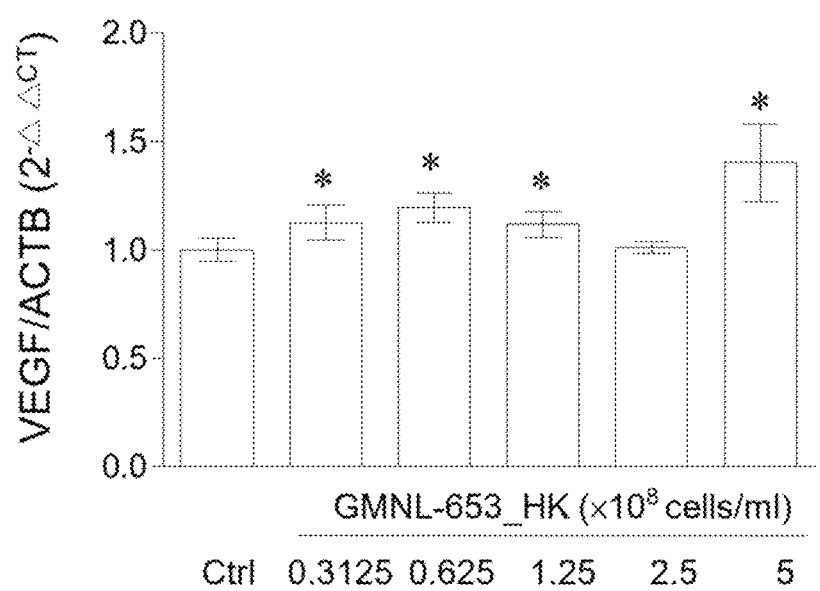
Figure 4C:
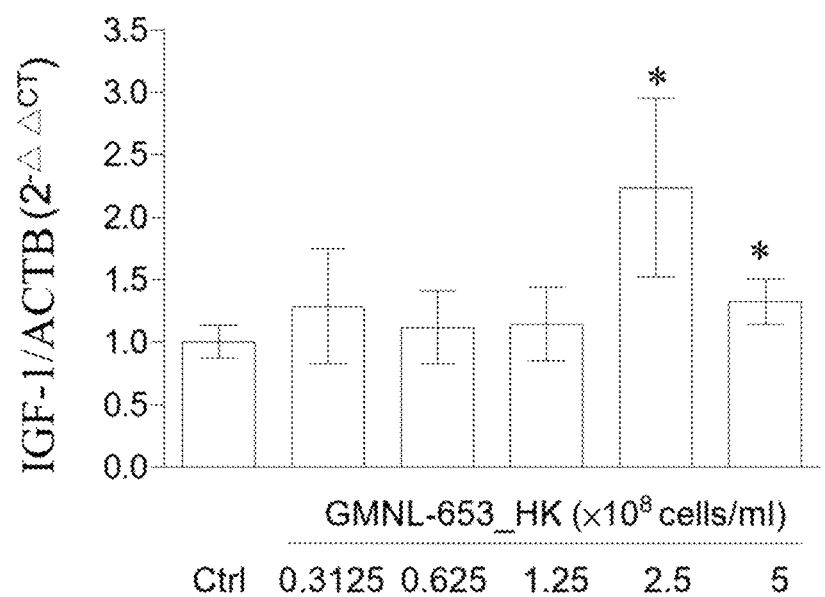

In addition, the effects of different doses of heat-killed GMNL-653 on human skin fibroblasts (Hs68) producing growth factors in the scalp, especially the factors related to hair growth, including IGF-1R (FIG. 3A), VEGF (FIG. 3B), IGF-1 (FIG. 3C), KGF (FIG. 3D), were evaluated. The results showed that the different doses of heat-killed GMNL-653 can promote the gene expressions of hair growth promoting factors, i.e., IGF-1R, VEGF, and KGF, in human skin fibroblasts (Hs68). Moreover, it can further promote the gene expressions of hair growth promoting factors, i.e., IGF-1R (FIG. 4A), VEGF (FIG. 4B), and IGF-1 (FIG. 4C), in human skin keratinocyte lines (HaCaT). Nevertheless, in the human skin keratinocyte cell lines, the expression of KGF was too low to be detected by Q-PCR method, and no result was presented. The above results showed that heat-killed *Lactobacillus paracasei* GMNL-653 has the effect on stimulating scalp hair regeneration.

Figure 5A:
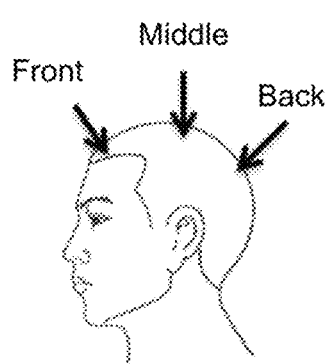
Figure 5A:
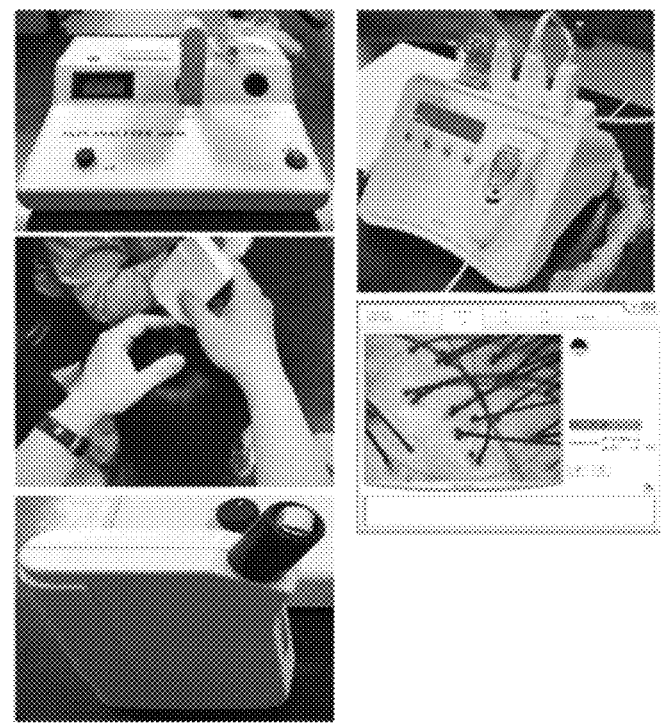
Figure 5B:
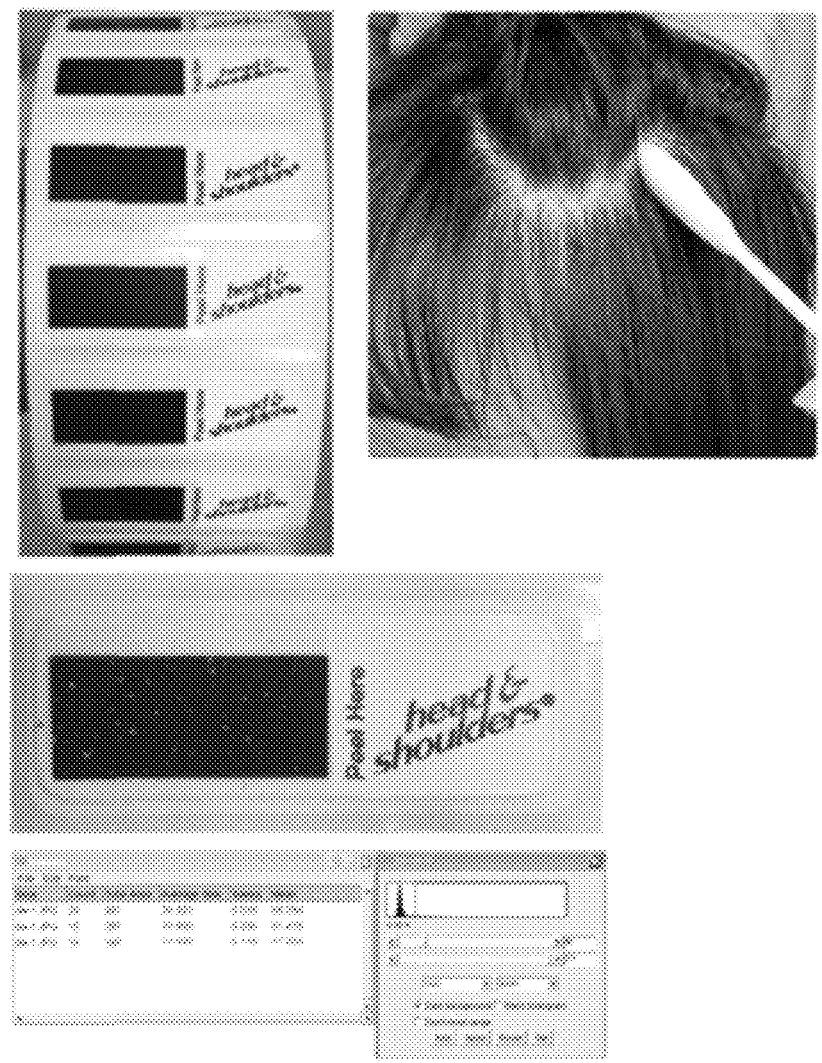

With reference to Table 2 below and FIGS. 5A and 5B, *Lactobacillus paracasei* GMNL-653 was further added to the shampoo (experimental group) for human clinical trials. There was a total of 22 subjects enrolled in this trial. The subjects first washed with the control group shampoo for 1 month, and then washed with the experimental group shampoo (containing the strain of *Lactobacillus paracasei* GMNL-653) for 4 months. Analysis of the scalp oiliness, dandruff, hair volume and scalp microbiota was conducted at each time point (Table 2).

TABLE 2

| | control group shampoo | | experimental group shampoo | | | |
|---|---|---|---|---|---|---|
| | 0 | 0.5 month | 1 month | 1.5 month | 2 month | 3 month | 5 month |
| scalp oil counts | yes | yes | yes | yes | yes | yes | yes |
| hair volume | yes | | yes | | | yes | yes |
| dandruff | yes | yes | yes | yes | yes | yes | yes |
| scalp microbiota | yes | | yes | | yes | | |

Figure 6A:
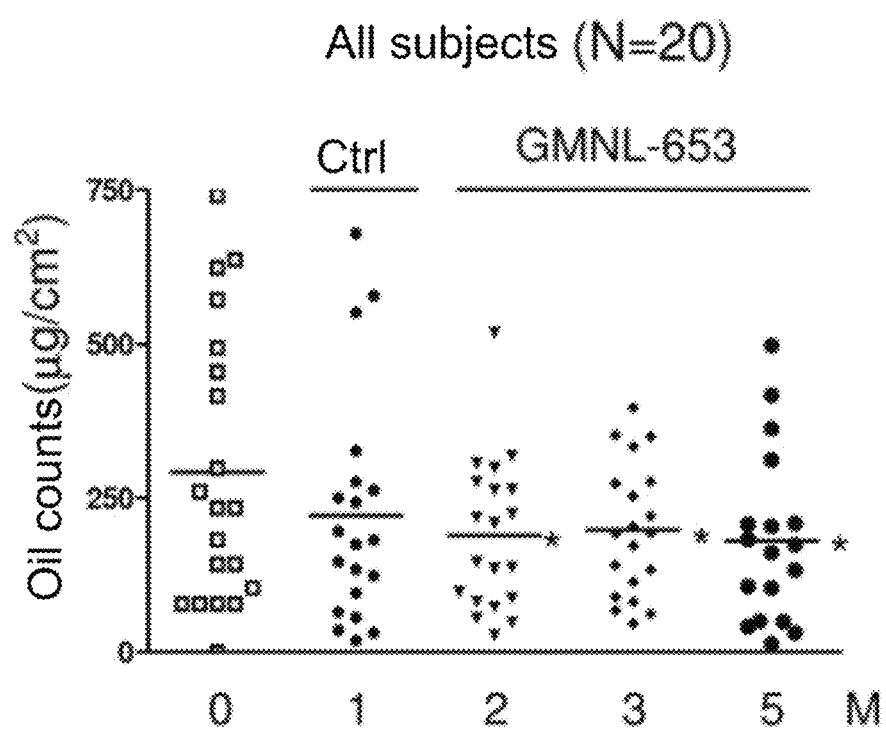
Figure 6B:
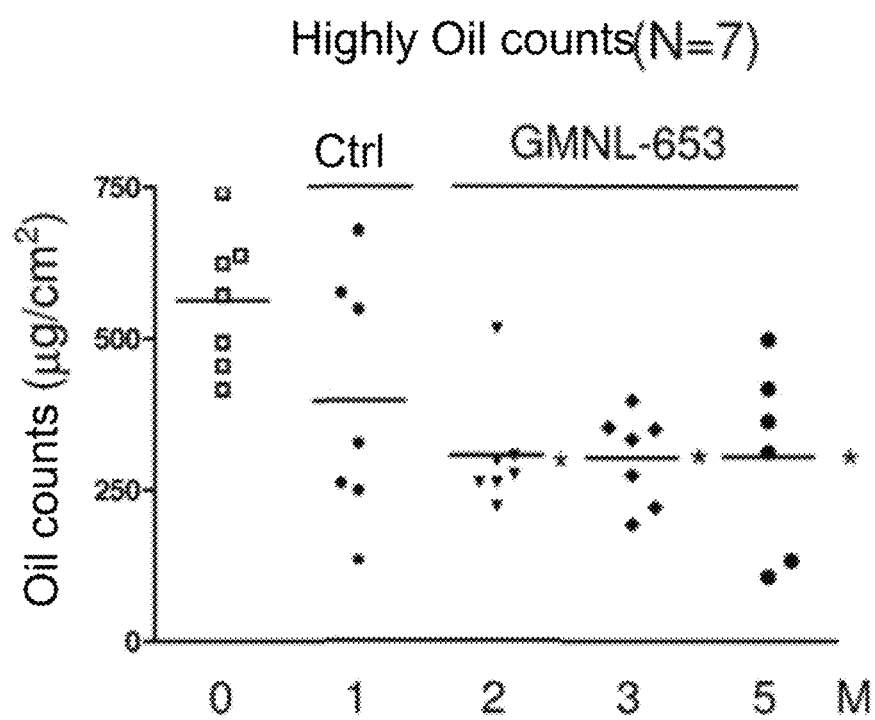
Figure 6C:
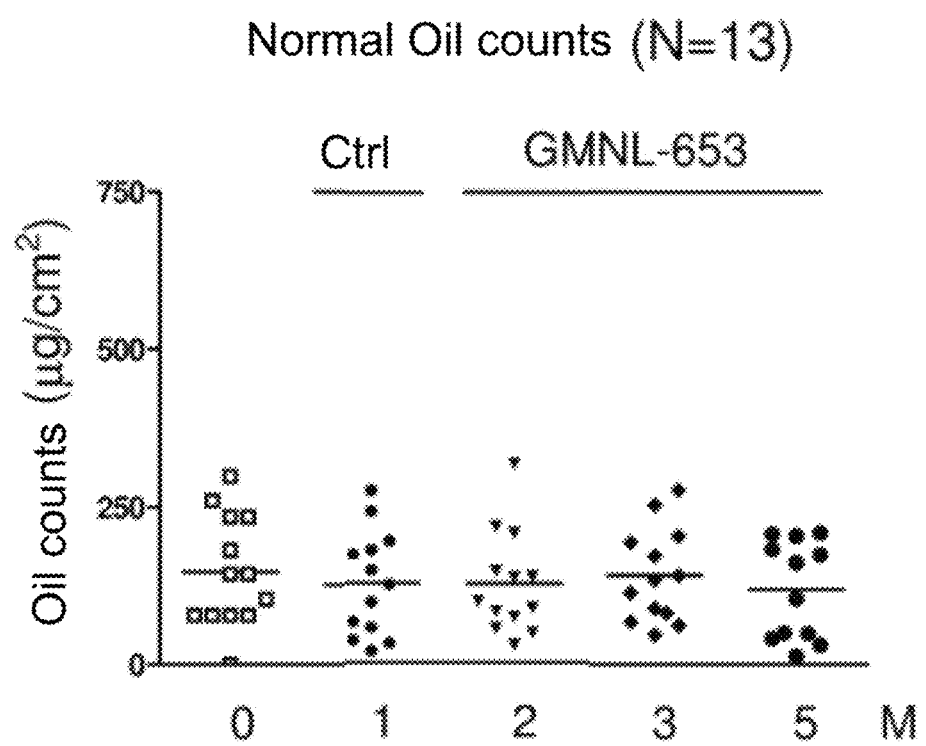

In terms of the scalp oil counts, all subjects were analyzed. There was a significant reduce in the oil counts of scalp after using the experimental group shampoo for 1-4 months compared with that at the beginning of the experiment (FIG. 6A). In addition, such effect was particularly significant in the subjects with the oily scalps (FIG. 6B), and there were slight changes respectively in the subjects with the normal and dry scalps. (FIG. 6C), indicating that GMNL-653 can adjust the oil count, depending on the scalp types.

Figure 7A:
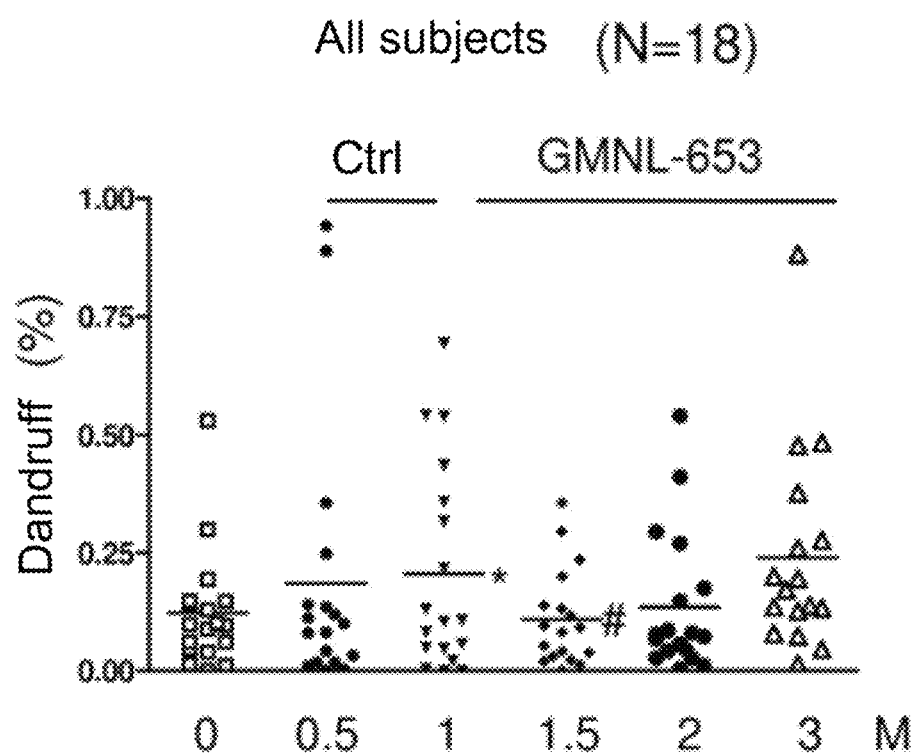
Figure 7B:
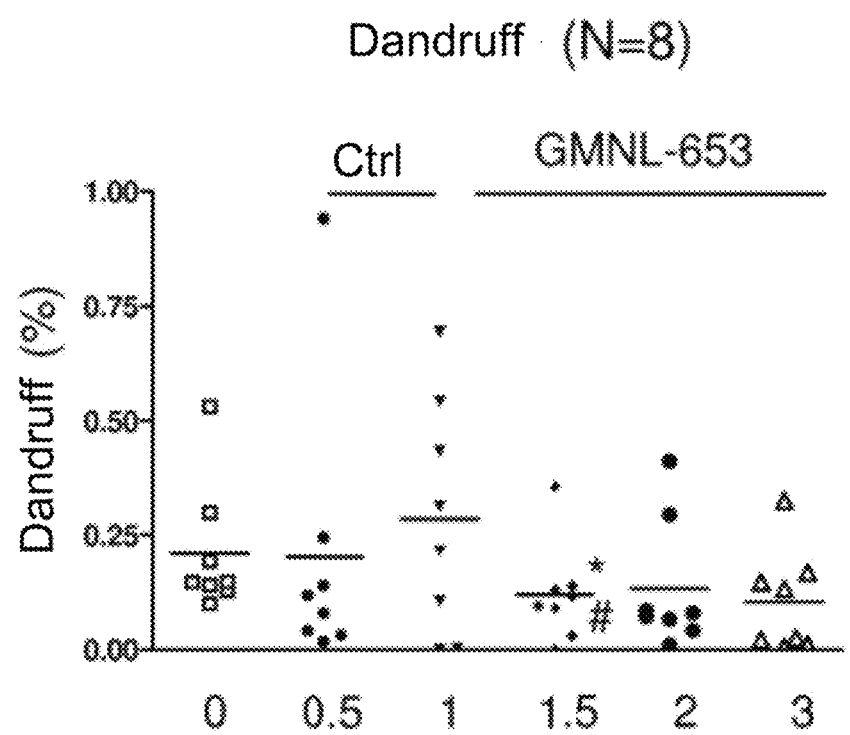
Figure 7C:
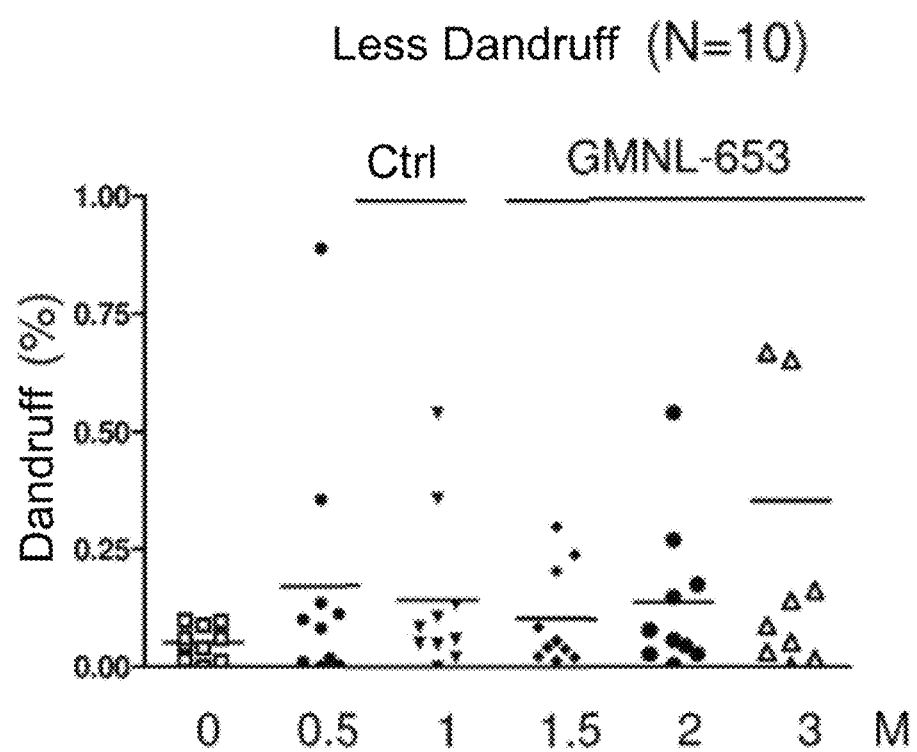

In terms of the dandruff, all subjects were analyzed. There was a slight increase in the dandruff after using the control group shampoo for 1 month compared with that at the beginning of the experiment. After using the experimental group shampoo for 0.5 months, production of the dandruff was significantly reduced (FIG. 7A). The subjects were divided into those with more dandruff and those with less dandruff for analysis, and the results showed that a significant improvement was achieved in those with more dandruff after using the experimental group shampoo for 0.5 months (FIG. 7B). However, there was little change in those with less dandruff (FIG. 7C).

Figure 8A:
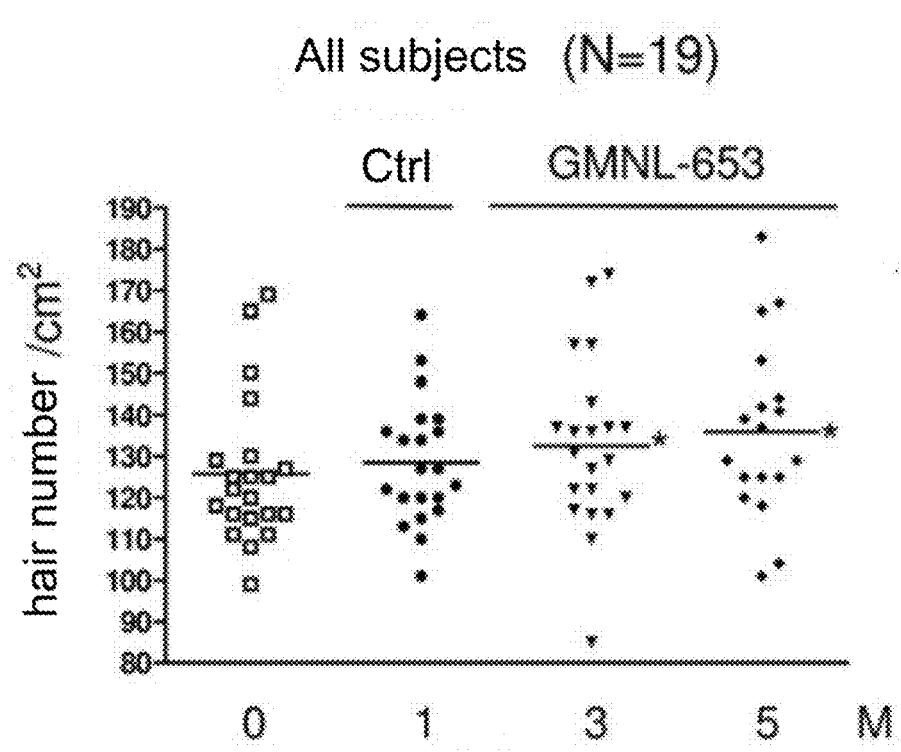
Figure 8B:
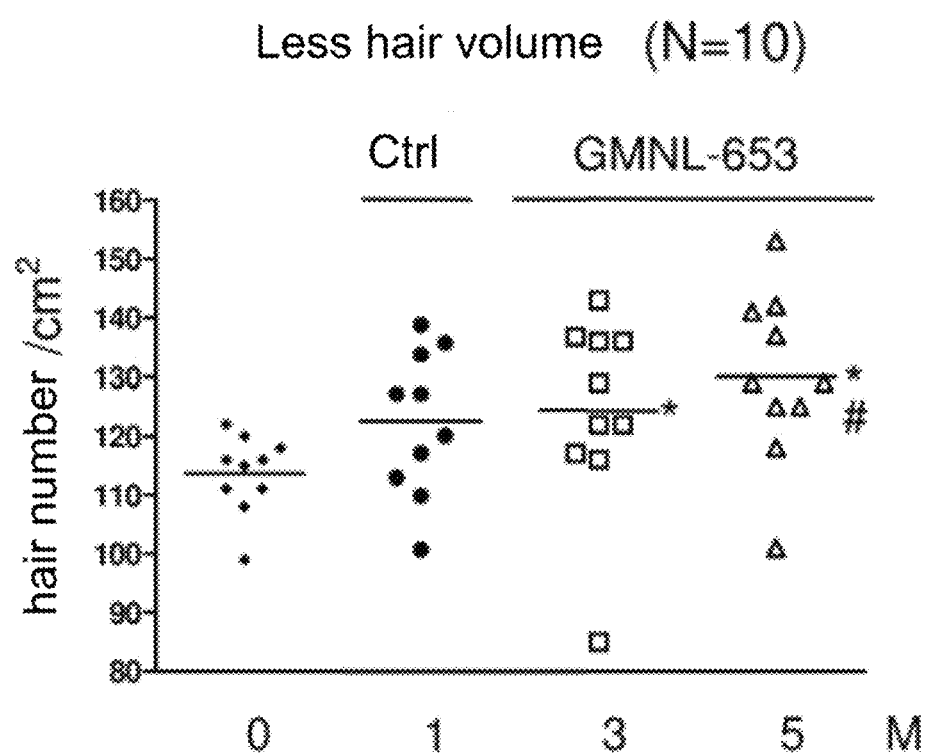
Figure 8C:
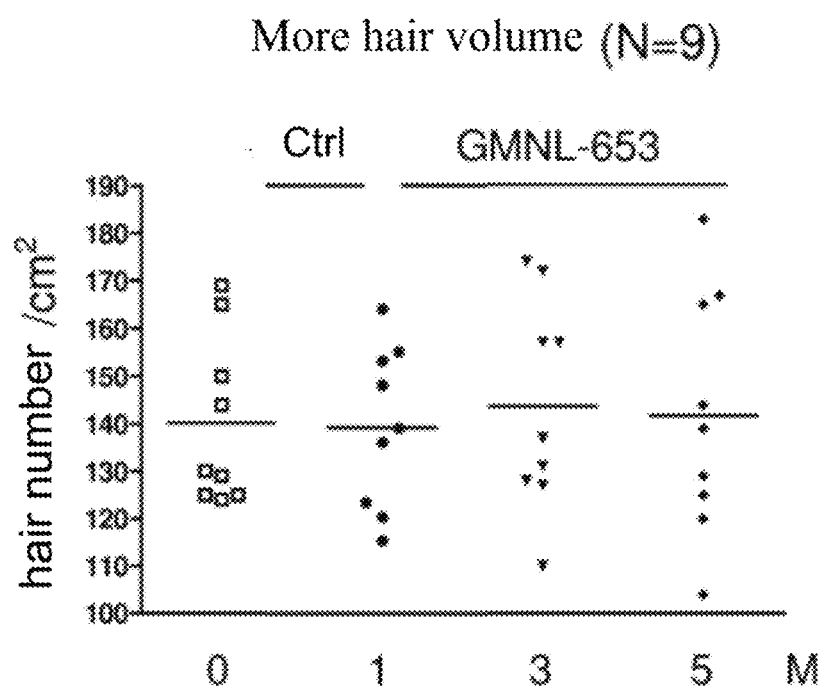

In terms of the hair volume, all subjects were analyzed. There was a significant increase in the hair volume after using the experimental group shampoo for 2-4 months compared with that at the beginning of the experiment (FIG. 8A). Especially for the subjects with less hair volume, the effect was particularly significant. When compared with 0 month (beginning of the experiment) or 1 month (1 month after using the control group shampoo), there was a significant increase in the hair volume in the subject with less hair volume after using the experimental group shampoo (FIG. 8B).

Figure 9A:
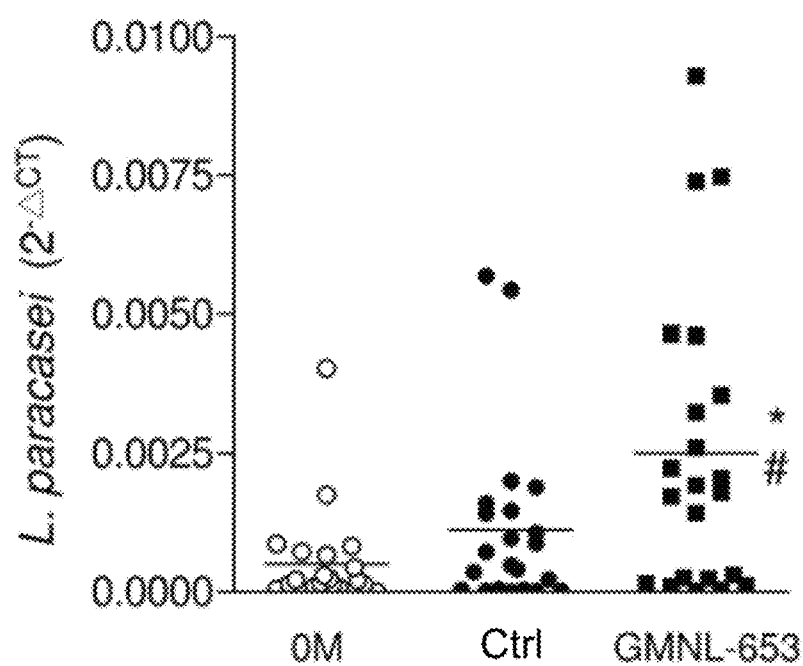
Figure 9B:
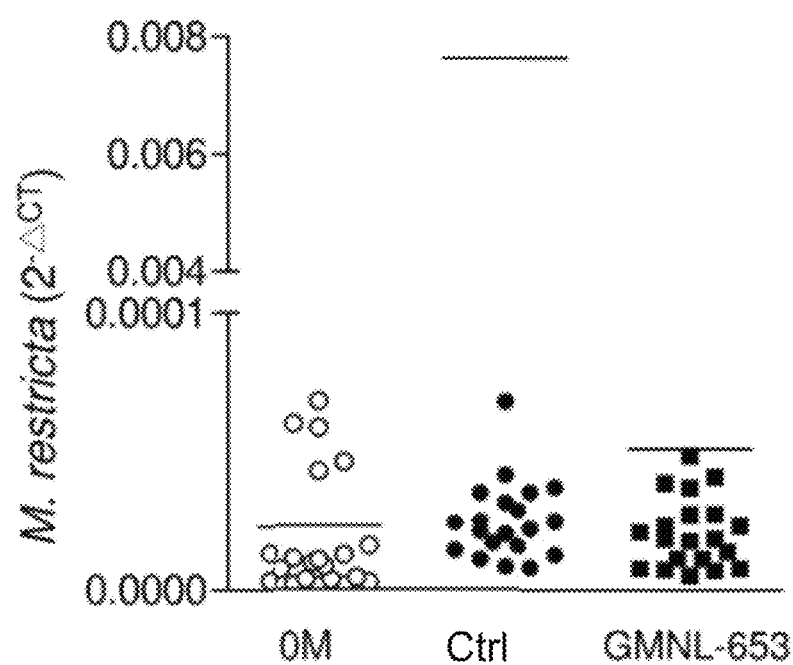
Figure 9C:
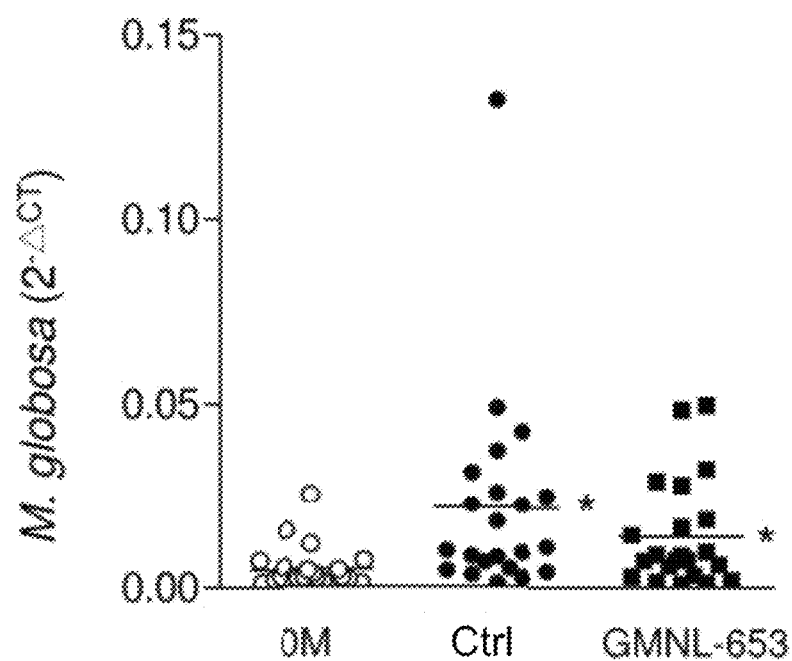

Scalp microbiota, including L. paracasei, Malassezia restricta (M. restricta), Malassezia globosa (M. globosa), Propionibacterium acnes (P. acnes), Staphylococcus epidermidis (S. epidermidis) was analyzed by Q-PCR. Compared with the starting point, the use of control group shampoo for 1 month can significantly increase the number of M. globosa and decreased the number of P. acnes on the scalps (FIGS. 9C and 9D), indicating that the control group shampoo can even cause changes in the microbiota of scalp. Compared with the starting point, the use of experimental group shampoo for 1 month can increase the numbers of L. paracasei and M. globosa and reduce the number of P. acnes on the scalps (FIGS. 9A, 9C and 9D), indicating that the experimental group shampoo can significantly increase the beneficial bacteria on the scalps, especially Lactobacillus paracasei, as shown in FIG. 9A.

Figure 9D:
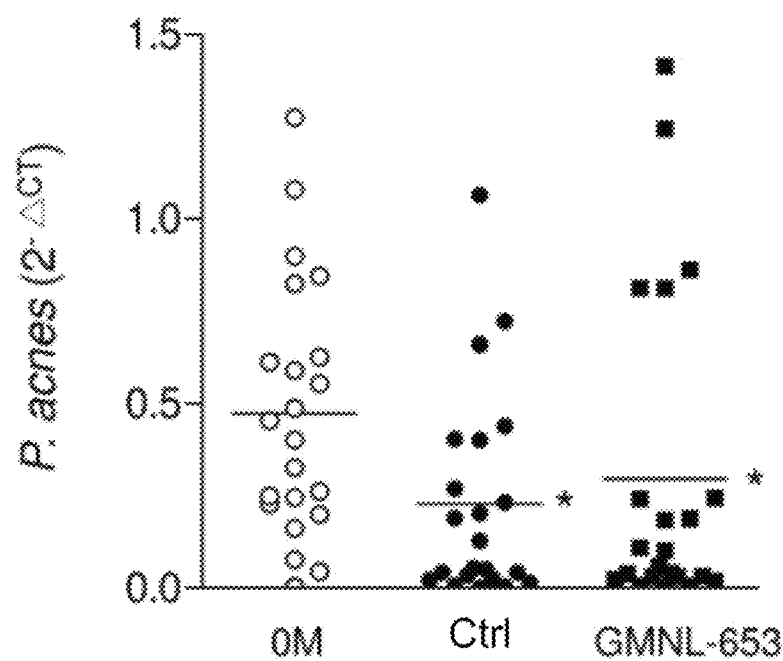
Figure 9E:
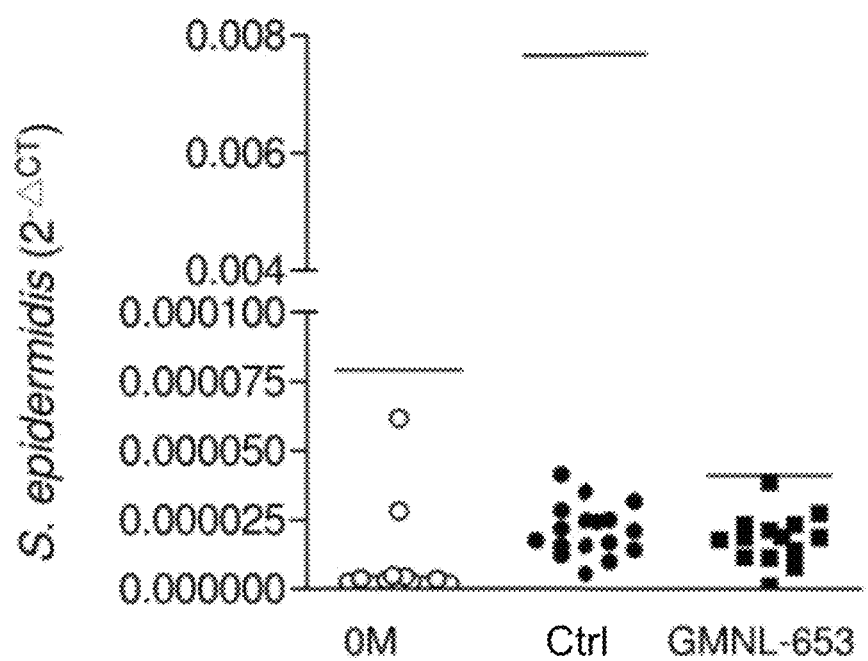
Figure 10A:
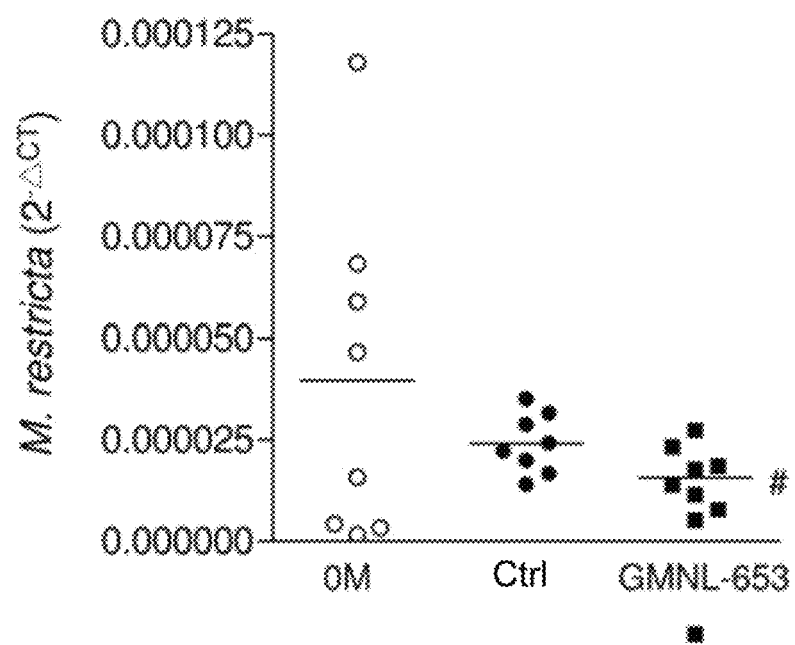
Figure 10B:
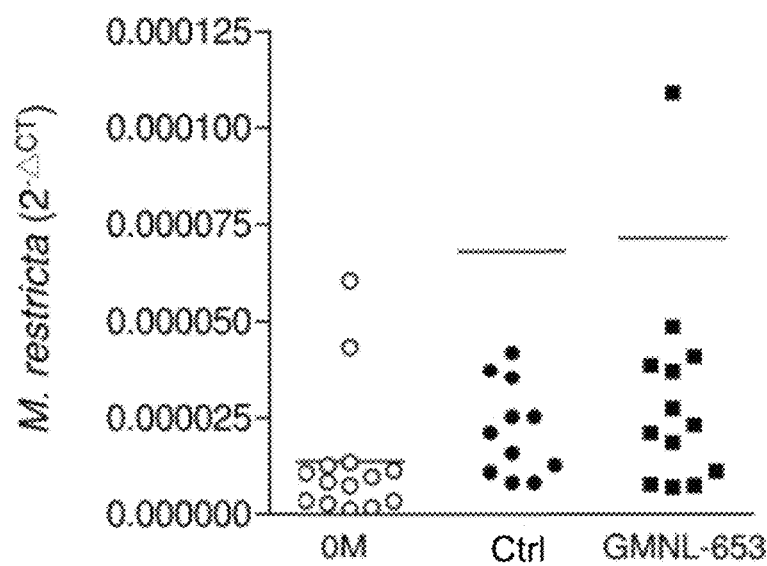
Figure 10C:
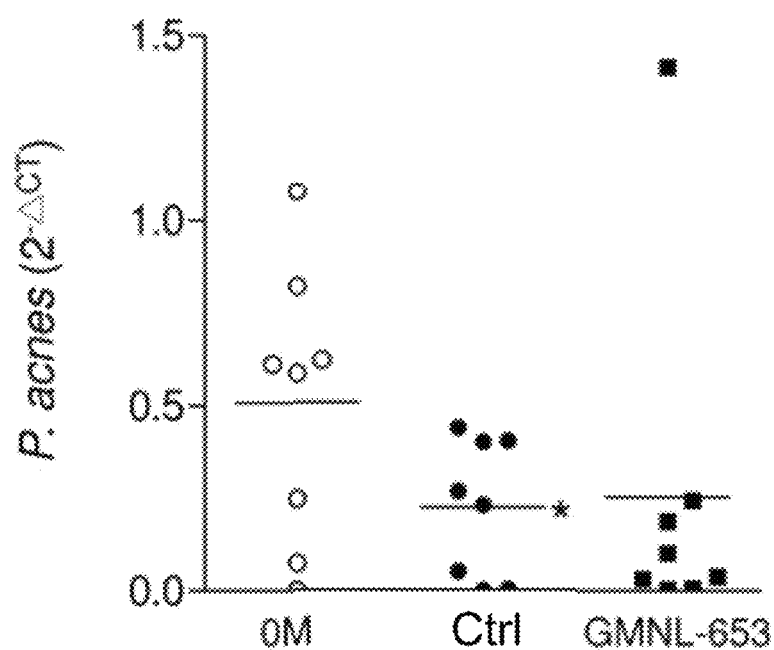
Figure 10D:
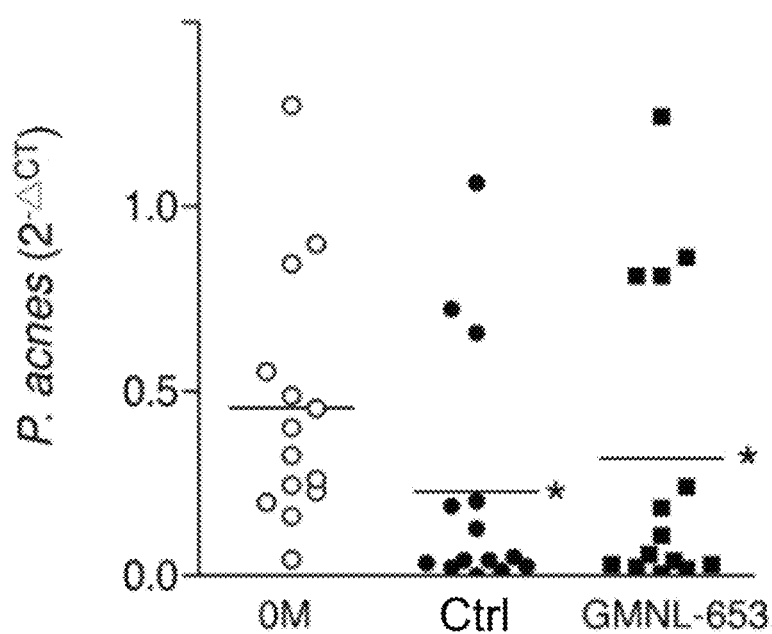
Figure 10E:
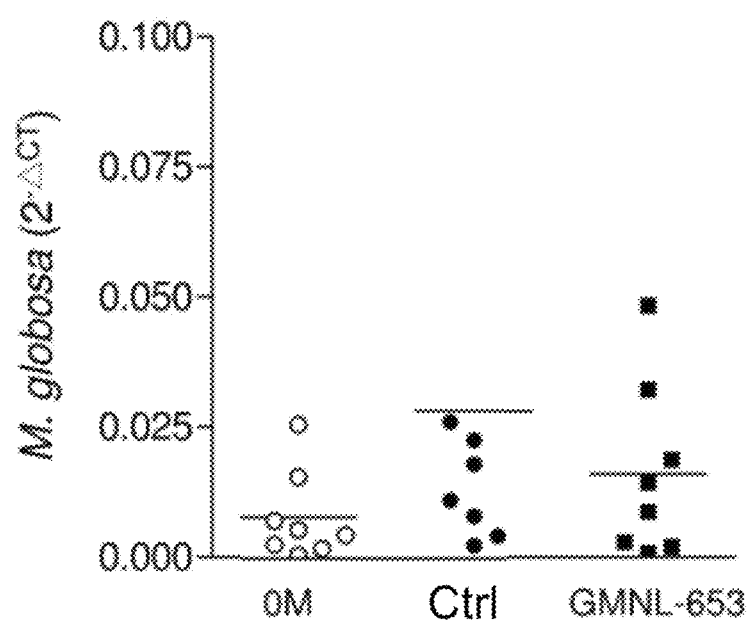
Figure 10F:
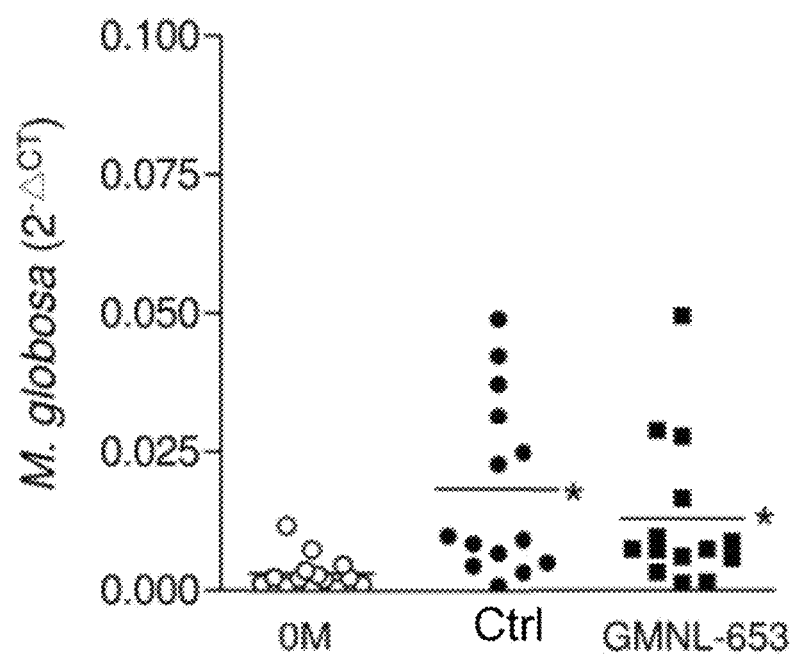

Furthermore, the lower number of P. acnes which are reportedly associated with an unhealthy scalp was also found at the beginning of the experiment (FIG. 9D). The subjects were divided into those with dandruff and those with less dandruff for analysis. It was found that the two groups have different changes in the microbiota after using the control group shampoo and the experimental group shampoo. It was found that in the group with dandruff, M. restricta on the scalps of those using the experimental group shampoo is significantly lower than those of using the control group shampoo (FIG. 10A). It is worth mentioning that previous studies have found that M. restricta is an important pathogen for massive production of dandruff.

Figure 11A:
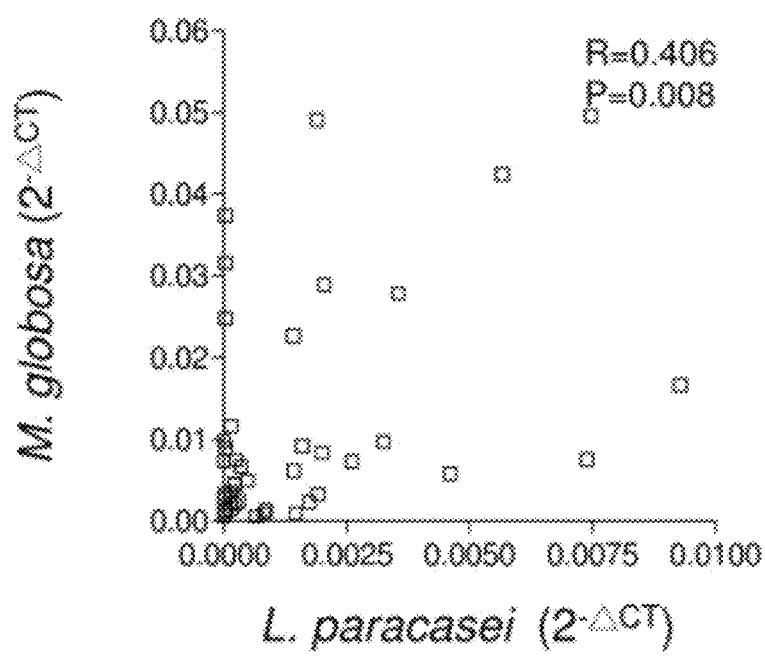
FIG. 11A to FIG. 11F show the correlation analysis of scalp microbiota changes and scalp status, wherein Pearson correlation of the contents of different strains (FIG. 11A-FIG. 11C), Pearson correlation of the contents of different strains and the hair volume (FIG. 11D, FIG. 11E), and Pearson correlation of the contents of *P. acnes* and the scalp oil counts (FIG. 11F) are analyzed by SPSS statistical software, in which R indicates correlation (a positive value indicating positive correlation, and a negative value indicating negative correlation), and P indicates the statistical difference.
Figure 11B:
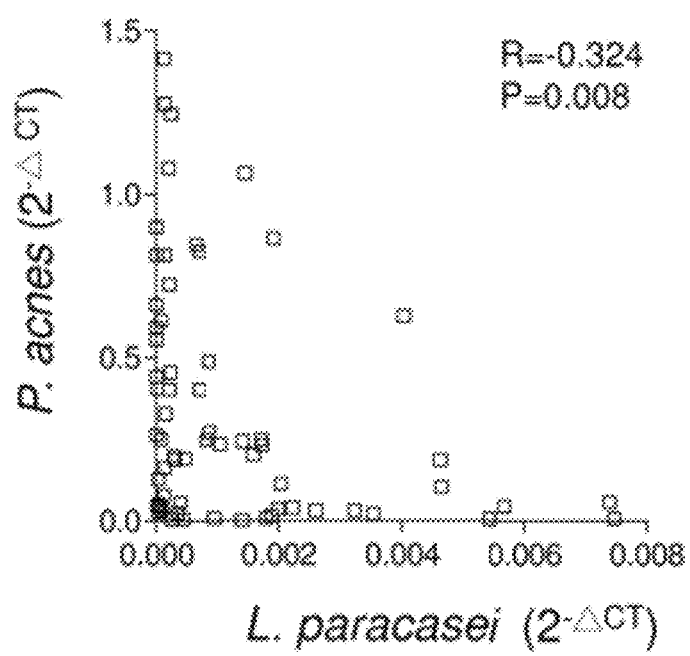
Figure 11C:
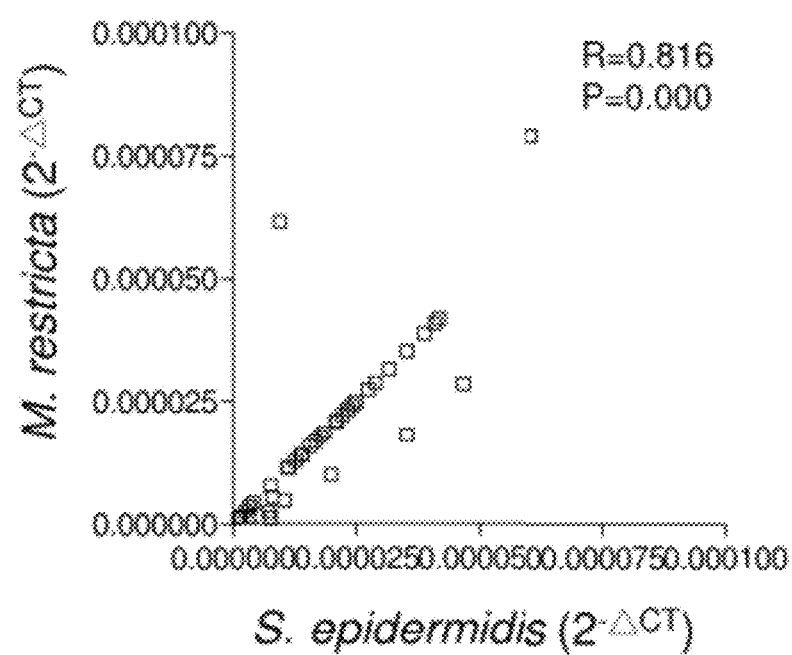

Furthermore, the data of Pearson correlation analysis showed that the content of Lactobacillus paracasei on the scalps was positively correlated with M. globosa (R=0.406, P=0.008) (FIG. 11A), but negatively correlated with P. acnes (R=−0.324, P=0.008) (FIG. 11B), indicating that Lactobacillus paracasei can change the distribution of the scalp microbiota.

Figure 11D:
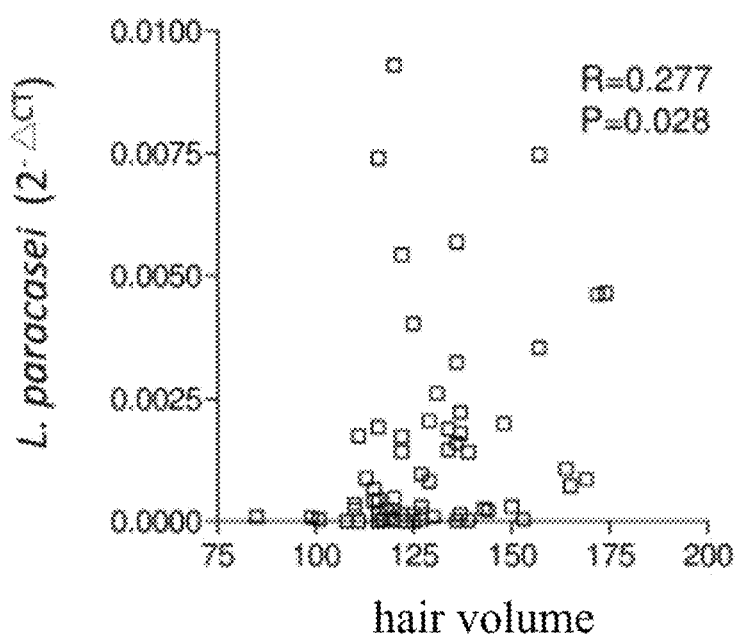
Figure 11E:
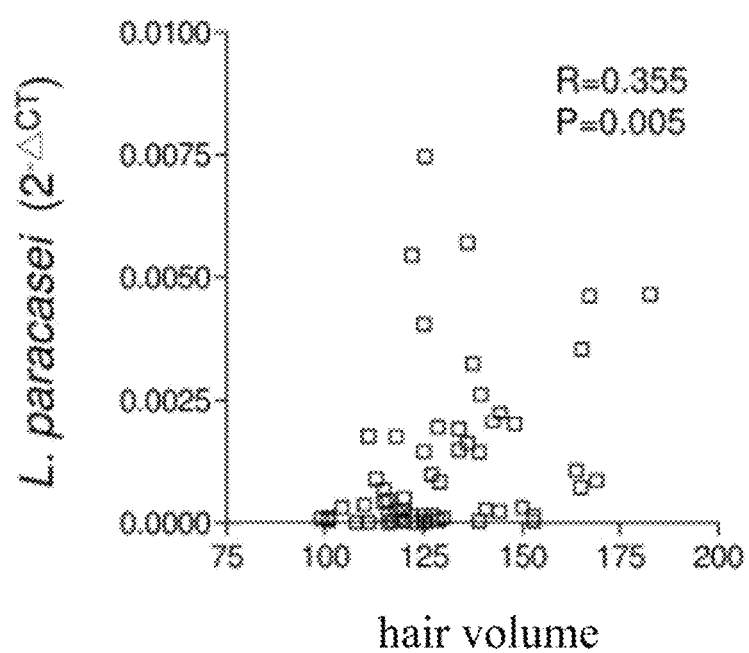
Figure 11F:
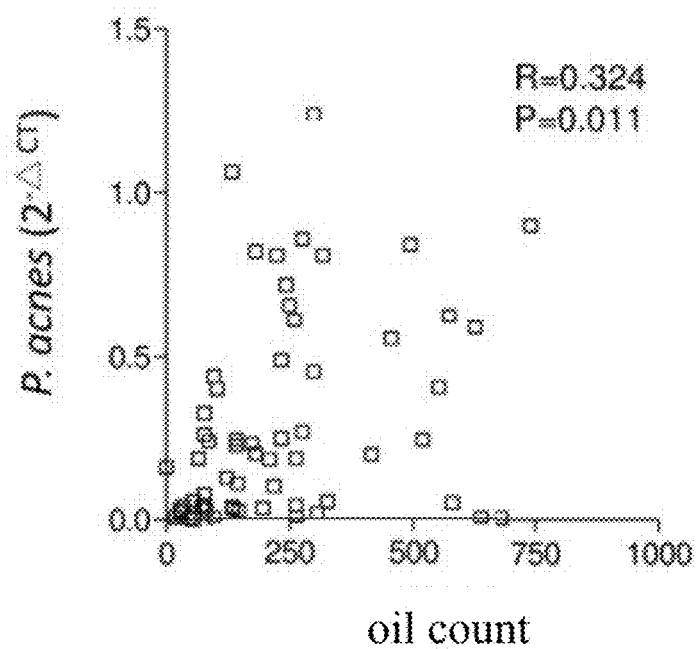

After analyzing the correlation between the microbiota and the change in the hair volume after using experimental group shampoo (containing the strain of Lactobacillus paracasei GMNL-653) for 2 or 4 months, it was found that the content of Lactobacillus paracasei was positively correlated with the hair volume (R=0.277, P=0.028 and R=0.355, P=0.005) (FIG. 11D and FIG. 11E). After analyzing the correlation between the microbiota and the change in the hair oil count, it was found that the content of P. acnes was positively correlated with the scalp oil count (R=0.324, P=0.011) (FIG. 11F). In summary, all the above results showed that the microbiota affected hair volume and scalp oil distribution indeed.

The above results showed that the lysates of Lactobacillus paracasei GMNL-653 inhibited aging of the scalps caused by peroxides and helped maintain a health scalp. In addition, the LTA on the cell surface of Lactobacillus paracasei GMNL-653 can inhibit the formations of the biofilms of M. furfur and S. aureus, so that the scalps can be protected from pathogenic bacteria, and a purpose of strengthening hair roots can be achieved. After using the shampoo (experimental group) containing the strain of Lactobacillus paracasei promoting hair growth of the present disclosure, it was found that Lactobacillus paracasei GMNL-653 can stay on the scalps and stimulate the scalps to secrete growth factors that stimulate hair regeneration, such as IGF-1, IGF-1R, VEGF, and KGF, and regulate the scalp microbiota, so as to maintain hair volume. In addition, the experimental data showed that a number of M. restricta on the scalps can be reduced by Lactobacillus paracasei GMNL-653, so that the effect of controlling dandruff can be achieved, and the effect of oil control can be achieved by reducing P. acnes on the scalps.

While the preferred embodiments of the present disclosure have been described above, it will be recognized and understood that various changes and modifications can be made, and the appended claims are intended to cover all such changes and modifications which may fall within the spirit and scope of the present disclosure.

SEQUENCE LISTING

<110> GENMONT BIOTECH INC.
<120> STRAIN OF LACTOBACILLUS PARACASEI FOR PROMOTING HAIR GROWTH, HAIR PRODUCT HAVING SAME, AND USE THEREOF
<130> TP211478-TW
<150> TW 110144288
<151> 2021-11-26
<160> 3
<170> PatentIn version 3.5
<210> 1
<211> 20
<212> DNA
<213> Artificial Sequence
<220>
<223> PAF primer
<400> 1
agagtttgat cctggctcag 20
<210> 2
<211> 18
<212> DNA
<213> Artificial Sequence
<220>
<223> 536R primer
<400> 2
gtattaccgc ggctgctg 18
<210> 3
<211> 523
<212> DNA
<213> Artificial Sequence
<220>
<223> Sequencing primer
<400> 3
cggaggcccc tatgatgggc gtcgtacgag ttctcgttga tgatcggtgc
    ttgcaccgag 60
attctcatgg aacgagtggc ggacgggtga gtaacacgtg ggtaacctgc
    ccttaagtgg 120
gggataacat ttggaaacag atgctaatac cgcatagatc ctgtaaccgc
    atggttcttg 180
gctgatagat ggcgtaagct atcgctgttg gatggacccg cggcgtatta
    tctagttggt 240
gaggtagtgg ctcaccgagg ccatgatacg tatccgagct gagaggttga
    tgggcgagtt 300
tgtgactgag acacgtccca aactactacg ggaggcagca gtagggaatc
    ttccacaatg 360
gacgcaagtc tgatggagca acgccgcgtg agtgaagaag gctttcgggt
    cgtaaaactc 420
tgttgttgga gaagaatggt cggcagagta actgttgtcg gcgtgacggt
    atccaaccag 480
aaagccacgg ctaactacgt gccagcagcc gggggtaat aca 523

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: PAF primer

<400> SEQUENCE: 1
agagtttgat cctggctcag					20

<210> SEQ ID NO 2
<211> LENGTH: 18
<212> TYPE: DNA
<213> ORGANISM: Artificial Sequence
<220> FEATURE:
<223> OTHER INFORMATION: 536R primer

<400> SEQUENCE: 2
gtattaccgc ggctgctg					18

<210> SEQ ID NO 3
<211> LENGTH: 523
<212> TYPE: DNA
<213> ORGANISM: Artificial Sequence
<220> FEATURE:
<223> OTHER INFORMATION: Sequencing primer

<400> SEQUENCE: 3
cggaggcccc tatgatgggc gtcgtacgag ttctcgttga tgatcggtgc ttgcaccgag      60
attctcatgg aacgagtggc ggacgggtga gtaacacgtg ggtaacctgc ccttaagtgg     120
gggataacat ttggaaacag atgctaatac cgcatagatc ctgtaaccgc atggttcttg     180
gctgatagat ggcgtaagct atcgctgttg gatggacccg cggcgtatta tctagttggt     240
gaggtagtgg ctcaccgagg ccatgatacg tatccgagct gagaggttga tgggcgagtt     300
tgtgactgag acacgtccca aactactacg ggaggcagca gtagggaatc ttccacaatg     360
gacgcaagtc tgatggagca acgccgcgtg agtgaagaag gctttcgggt cgtaaaactc     420
tgttgttgga gaagaatggt cggcagagta actgttgtcg gcgtgacggt atccaaccag     480
aaagccacgg ctaactacgt gccagcagcc gggggtaat aca                       523

What is claimed is:

1. A method for promoting hair growth by increasing growth factors in epidermis, comprising a step of administering dead cells of *Lactobacillus paracasei* GMNL-653 onto skin of a subject who needs to increase hair volume at a dose of $1.25 \times 10^8$ to $5 \times 10^8$ cells/ml/day, and the *Lactobacillus paracasei* GMNL-653 was deposited at the China Center for Type Culture Collection located at Wuhan University, Wuhan 430072, P.R. China on Apr. 25, 2016 under an accession number CCTCC NO. M 2016226.

2. The method as claimed in claim 1, wherein a number of days of administration ranges from 1 to 3 months.

\* \* \* \* \*